United States Patent
Yasui et al.

(10) Patent No.: US 6,920,751 B2
(45) Date of Patent: Jul. 26, 2005

(54) APPARATUS AND METHOD FOR DETECTING FAILURE OF EXHAUST GAS SENSOR

(75) Inventors: Yuji Yasui, Wako (JP); Hiroshi Kitagawa, Wako (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 78 days.

(21) Appl. No.: 10/437,457

(22) Filed: May 14, 2003

(65) Prior Publication Data

US 2004/0010364 A1 Jan. 15, 2004

(30) Foreign Application Priority Data

May 16, 2002 (JP) ........................................ 2002-141617

(51) Int. Cl.[7] ................................................. F01N 3/00
(52) U.S. Cl. ........................... 60/277; 60/274; 60/276; 73/23.31
(58) Field of Search .......................... 60/274, 276, 277; 73/23.31, 23.32, 118.1; 204/401

(56) References Cited

U.S. PATENT DOCUMENTS 5,359,853 A * 11/1994 Shimizu ...................... 60/276

2003/0131586 A1 * 7/2003 Kato et al. ................... 60/274

FOREIGN PATENT DOCUMENTS

JP          2812252         8/1998

* cited by examiner

Primary Examiner—Thomas Denion
Assistant Examiner—Diem Tran
(74) Attorney, Agent, or Firm—Squire, Sanders & Dempsey L.L.P.

(57) ABSTRACT

An apparatus for detecting a failure of an exhaust gas sensor disposed downstream of a catalyst converter in an exhaust manifold is provided. The apparatus comprises a control unit. The control unit determines a ratio between an amplitude value of a first output of the exhaust gas sensor and an amplitude value of a second output of an air-fuel ratio sensor. The air fuel ratio sensor disposed upstream of the catalyst converter. The control unit detects a failure of the exhaust gas sensor based on the ratio. In one embodiment, a statistical process using a successive least squares method is applied to the ratio. The control unit detects a failure of the exhaust gas sensor based on the statistically processed ratio. In another embodiment, the statistical process is applied to both the output of the exhaust gas sensor and the output of the air-fuel ratio sensor. The control unit detects a failure of the exhaust gas sensor based on a ratio between the statistically processed outputs of the exhaust gas sensor and the air-fuel ratio sensor.

38 Claims, 16 Drawing Sheets

Fig. 2
(a)
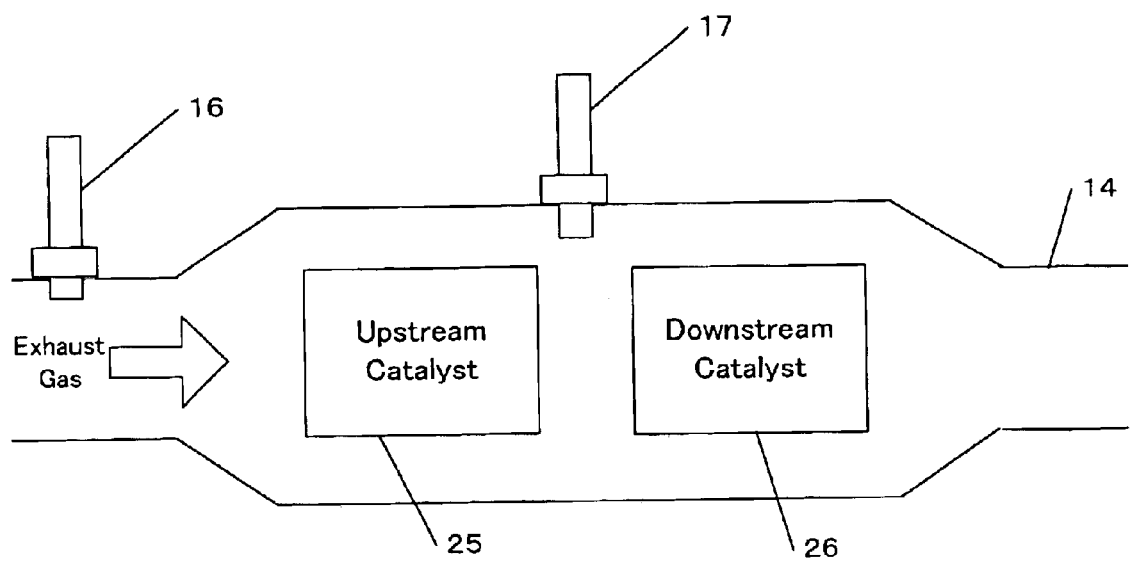
(b)
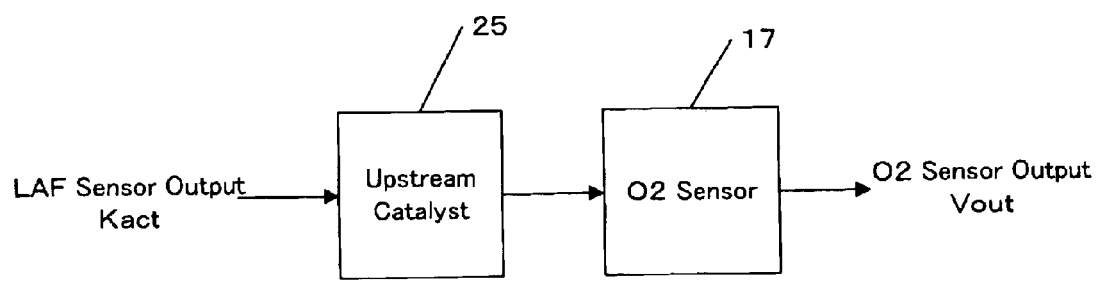

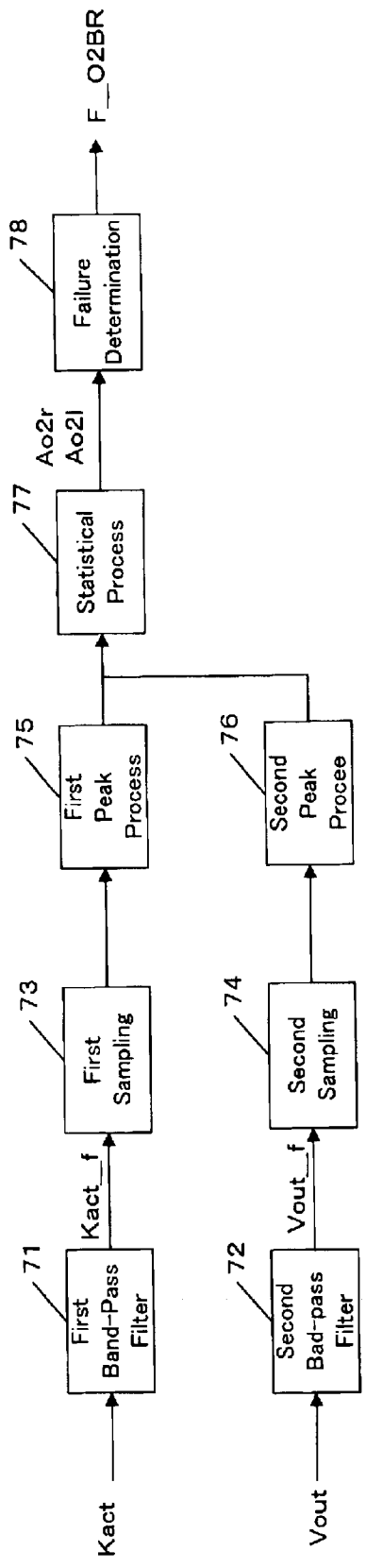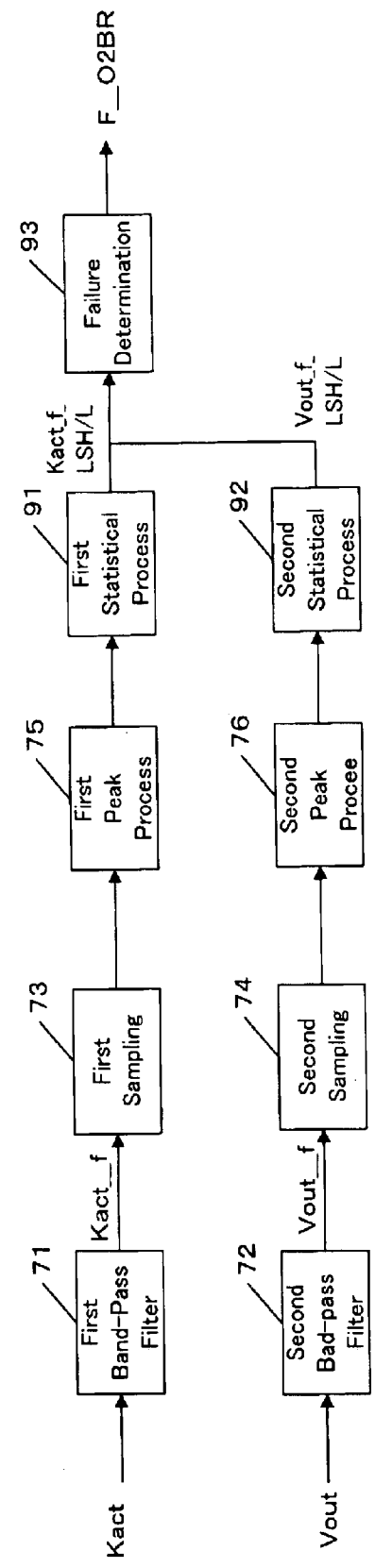

APPARATUS AND METHOD FOR DETECTING FAILURE OF EXHAUST GAS SENSOR

BACKGROUND OF THE INVENTION

1. Technical Field

The present invention relates to an apparatus for detecting a failure of an exhaust gas sensor provided in an exhaust system of an internal combustion engine.

2. Description of Related Art

A catalyst converter for purifying exhaust gas is provided in an exhaust system of an internal combustion engine of a vehicle. When the air-fuel ratio of air-fuel mixture introduced into the engine is lean, the catalyst converter oxidizes HC and CO with excessive oxygen included in the exhaust gas. When the air-fuel ratio is rich, the catalyst converter reduces Nox with HC and CO. When the air-fuel ratio is in the stoichiometric air-fuel ratio region, HC, CO and Nox are simultaneously and effectively purified.

An exhaust gas sensor is provided downstream of the catalyst converter. The exhaust gas sensor detects the concentration of oxygen included in the gas that is discharged into the exhaust system. The detection value of the exhaust gas sensor is used for various control of the internal combustion engine. If response of the exhaust gas sensor deteriorates, the internal combustion engine may not be appropriately controlled, which may cause deterioration in the operating state of the engine.

Japanese Patent No. 2812252 discloses a method for detecting an abnormal state of an exhaust gas sensor based on the differential of the output of the exhaust gas sensor. When the number of times that the differential of an output of the exhaust gas sensor is great is less than a predetermined value, it is determined that the exhaust gas sensor is in an abnormal state. The method is based on the knowledge that the time-differential of the sensor output is often far from zero when the exhaust gas sensor is normal, while the time-differential of the sensor output is always close to zero when the exhaust gas sensor is faulty.

Since the catalyst converter and the exhaust gas sensor are disposed in series, the time-differential of the output of the exhaust gas sensor is influenced by delay characteristics (low pass characteristics) of the catalyst. That is, the output of the exhaust gas sensor varies according to the degree of deterioration of the catalyst. In the above conventional scheme of analyzing variations in the time-differential of the output of the exhaust gas sensor, it is difficult to determine whether such variations are caused by changes in response characteristics of the catalyst or by changes in response characteristics of the exhaust gas sensor. Therefore, there is a need for an apparatus and a method capable of detecting a failure of an exhaust gas sensor as distinguished from deterioration of catalyst.

SUMMARY OF THE INVENTION

According to one aspect of the present invention, an apparatus for detecting a failure of an exhaust gas sensor disposed downstream of a catalyst converter in an exhaust manifold of an engine is provided. The apparatus comprises a control unit configured to determine a ratio between an amplitude value of a first output of the exhaust gas sensor and an amplitude value of a second output of an air-fuel ratio sensor. The air fuel ratio sensor is disposed upstream of the catalyst converter. The control unit detects a failure of the exhaust gas sensor based on the ratio.

An output of the exhaust gas sensor varies according to the air-fuel ratio, which is detected by the air-fuel ratio sensor. In the invention, since a failure of the exhaust gas sensor is detected based on the ratio between the amplitude of an output of the exhaust gas sensor and the amplitude of an output of the air-fuel ratio sensor, the failure can be stably detected even if the air-fuel ratio varies.

The air-fuel ratio does not need to be manipulated for the purpose of detecting a failure of the exhaust gas sensor. The failure detection can be done without increasing the amount of deleterious substances in the exhaust gas, which would otherwise be produced from manipulation of the air-fuel ratio for the purpose of the failure detection.

According to another aspect of the present invention, a first output having an amplitude value greater than a predetermined value is selected from outputs of the exhaust gas sensor. A second output having an amplitude value greater than a predetermined value is selected from outputs of the air-fuel ratio sensor. A ratio between the amplitude value of the selected first output and the amplitude value of the selected second output is determined to detect a failure of the exhaust gas sensor. According to the invention, a variation of the air-fuel ratio with which a failure of the exhaust sensor can be significantly detected is acquired by the air-fuel ratio sensor. By evaluating the output of the exhaust gas sensor corresponding to the acquired variation of the air-fuel ratio, the state of the exhaust gas sensor can be determined with better accuracy.

According to another aspect of the present invention, a first output having a local maximum amplitude value is selected from outputs of the exhaust gas sensor. A second output having a local maximum amplitude value is selected from outputs of the air-fuel ratio sensor. A ratio between the local maximum amplitude value selected for the first output and the local maximum amplitude value selected for the second output is determined to detect a failure of the exhaust gas sensor.

According to another aspect of the present invention, outputs of the exhaust gas sensor are sampled. A first sample having a local maximum amplitude value is identified from the samples obtained from the exhaust gas sensor. Samples in the vicinity of the first sample are also selected. A first set includes the first sample and the selected samples in the vicinity of the first sample. Similarly, outputs of the air-fuel ratio sensor are sampled. A second sample having a local maximum amplitude value is identified from the samples obtained from the air-fuel ratio sensor. Samples in the vicinity of the second sample are also selected. A second set includes the second sample and the selected samples in the vicinity of the second sample. A ratio is determined based on the first and second sets of samples.

There is a high correlation between the local maximum amplitude value of the output of the air-fuel ratio sensor and the local maximum amplitude value of the output of the exhaust gas sensor. A failure of the exhaust gas sensor can be detected based on a pair of the local maximum amplitude values. By selecting samples in the vicinity of the local maximum amplitude values, a failure of the exhaust gas sensor can be detected based on some pairs of the output of the air-fuel ratio sensor and the output of the exhaust gas sensor that have a high correlation. A temporal correlation between the output of the air-fuel ratio sensor and the output of the exhaust gas sensor is influenced by the operating state of the engine. Correlating both the output of the exhaust gas sensor and the output of the air-fuel ratio sensor can reduce such influence.

According to another aspect of the present invention, a statistical process is applied to the ratio between the amplitude value of the first output of the exhaust gas sensor and the amplitude value of the second output of the air-fuel ratio sensor. The statistical process includes a successive least squares method. A failure of the exhaust gas sensor is detected based on the statistically processed ratio.

According to another aspect of the present invention, the statistical process is applied to both the first output of the exhaust gas sensor and the second output of the air-fuel ratio sensor. The statistical process includes a successive least squares method. A ratio between the statistically processed first output and the statistically processed second output is determined. A failure of the exhaust gas sensor is detected based on the ratio.

The output of the air-fuel ratio sensor and the output of the exhaust gas sensor are influenced by noise and the operating state of the engine. By carrying out the statistical process using the successive least squares method, such influence on the failure detection can be reduced.

According to another aspect of the present invention, the first output of the exhaust gas sensor and the second output of the air-fuel ratio sensor are acquired when a vehicle is at cruise. The use of the sensor outputs obtained when a vehicle on which the engine is mounted is at cruise improves the accuracy of the failure detection.

According to another aspect of the present invention, the first output of the exhaust gas sensor and the second output of the air-fuel ratio sensor are obtained when the engine is in a predetermined operating state. The output of the exhaust gas sensor varies according to the operating state of the engine. By establishing a condition that the failure detection is performed under a predetermined operating state, such variations are suppressed, thereby improving the accuracy of the failure detection.

According to another aspect of the present invention, the apparatus for detecting a failure of the exhaust gas sensor further comprises a filter for filtering the first output of the exhaust gas sensor and the second output of the air-fuel ratio sensor. A ratio between the filtered first output and the filtered second output is determined. A failure of the exhaust gas sensor is detected based on the ratio. According to the invention, since the filtering process is applied to both the first and second outputs of the exhaust gas sensor and the air-fuel ratio sensor, influence by noise and influence by deterioration of the catalyst on the sensor outputs are reduced, thereby improving the accuracy of the failure detection.

According to another aspect of the present invention, the filtering process is carried out using a band-pass filter. It is preferable that the filtering process is carried out using a filter having characteristics of passing frequency components that are influenced by deterioration of the exhaust gas sensor and that are different from frequency components influenced by deterioration of the catalyst. Thus, frequency components influenced by deterioration of the catalyst are removed. Frequency components influenced by deterioration of the exhaust gas sensor are passed.

BRIEF DESCRIPTION OF THE DRAWINGS

FIG. 2 is a view of layout of a catalyst converter and an exhaust gas sensor according to one embodiment of the present invention.

FIG. 11 is a functional block diagram for a failure detection apparatus in accordance with a first embodiment of the present invention.

FIG. 13 is a functional block diagram for a failure detection apparatus in accordance with a second embodiment of the present invention.

DETAILED DESCRIPTION OF THE PREFERRED EMBODIMENTS

Structure of Internal Combustion Engine and Controller

Figure 1:
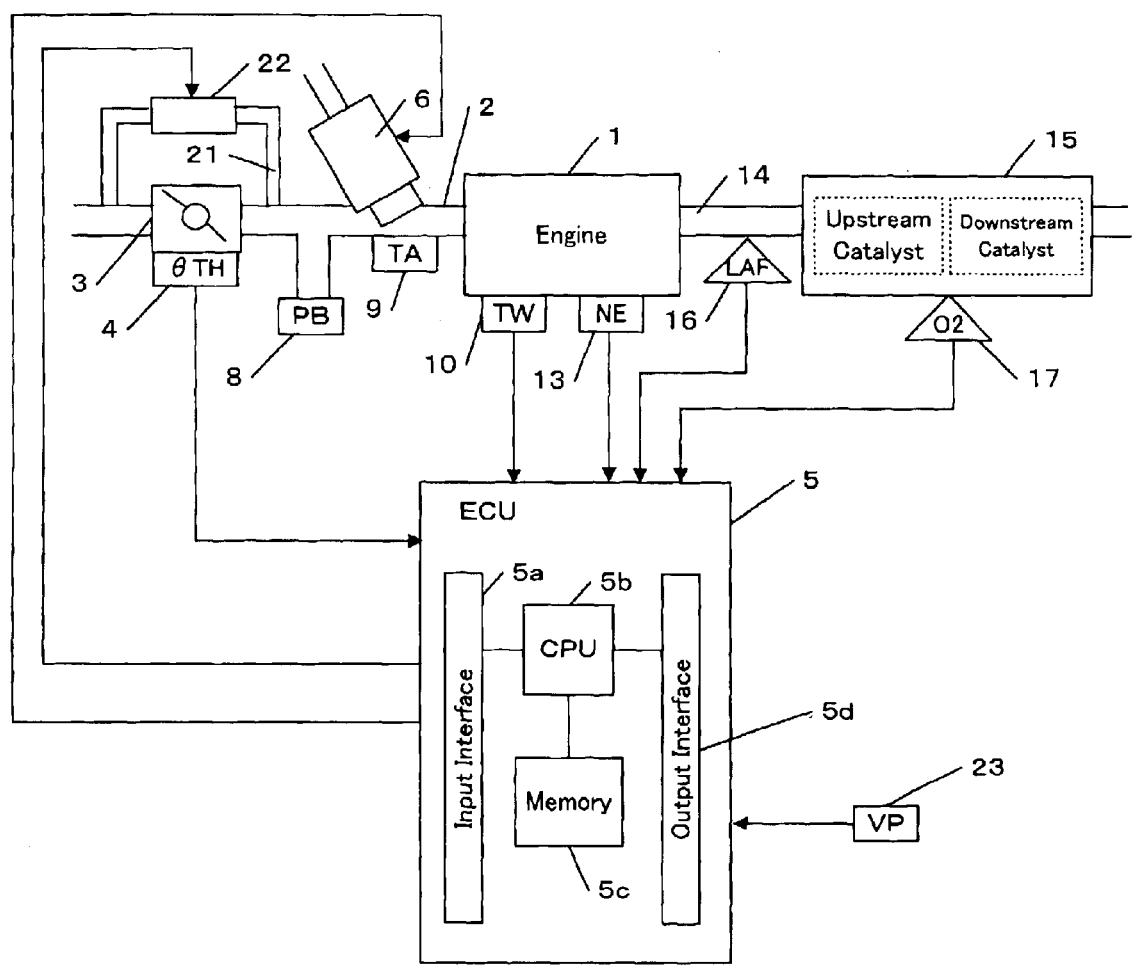
FIG. 1 is a schematic view of an internal combustion engine and its controller according to one embodiment of the present invention.

Preferred embodiments of the present invention will be described referring to the attached drawings. FIG. 1 is a block diagram showing a controller of an internal-combustion engine (hereinafter referred to as an engine) in accordance with one embodiment of the invention.

An electronic control unit (hereinafter referred to as an ECU) 5 comprises an input interface 5a for receiving data sent from each part of the engine 1, a CPU 5b for carrying out operations for controlling each part of the engine 1, a storage device 5c including a read only memory (ROM) and a random access memory (RAM), and an output interface 5d for sending control signals to each part of the engine 1. Programs and various data for controlling each part of the vehicle are stored in the ROM. A program for performing a failure detection process according to the invention, data and tables used for operations of the program are stored in the ROM. The ROM may be a rewritable ROM such as an EEPROM. The RAM provides work areas for operations by the CPU 5a, in which data sent from each part of the engine 1 as well as control signals to be sent out to each part of the engine 1 are temporarily stored.

The engine is, for example, an engine equipped with four cylinders. An intake manifold 2 is connected to the engine 1. A throttle valve 3 is disposed upstream of the intake manifold 2. A throttle valve opening (θTH) sensor 4, which is connected to the throttle valve 3, outputs an electric signal corresponding to an opening angle of the throttle valve 3 and sends it to the ECU 5.

A bypass passage 21 for bypassing the throttle valve 3 is provided in the intake manifold 2. A bypass valve 22 for controlling the amount of air to be supplied into the engine 1 is provided in the bypass passage 21. The bypass valve 22 is driven in accordance with a control signal from the ECU 5.

A fuel injection valve 6 is provided for each cylinder at an intermediate point in the intake manifold 2 between the engine 1 and the throttle valve 3. The fuel injection valve 6 is connected to a fuel pump (not shown) to receive fuel supplied from a fuel tank (not shown). The fuel injection valve 6 is driven in accordance with a control signal from the ECU 5.

An intake manifold pressure (Pb) sensor 8 and an outside air temperature (Ta) sensor 9 are mounted in the intake manifold 2 downstream of the throttle valve 3. The detected intake manifold pressure Pb and outside air temperature Ta are sent to the ECU 5.

An engine water temperature (TW) sensor 10 is attached to the cylinder peripheral wall, which is filled with cooling water, of the cylinder block of the engine 1. The temperature of the engine cooling water detected by the TW sensor is sent to the ECU 5.

A rotational speed (Ne) sensor 13 is attached to the periphery of the camshaft or the periphery of the crankshaft (not shown) of the engine 1, and outputs a CRK signal pulse at a predetermined crank angle cycle (for example, a cycle of 30 degrees) that is shorter than a TDC signal pulse cycle issued at a crank angle cycle associated with a TDC position of the piston. The CRK pulses are counted by the ECU 5 to determine the rotational speed Ne of the engine 1.

An exhaust manifold 14 is connected to the engine 1. The engine 1 discharges exhaust gas through the exhaust manifold 14. A catalyst converter 15 removes deleterious substances such as HC, CO, and Nox included in exhaust gas flowing through the exhaust manifold 14. The catalyst converter 15 comprises two catalysts, an upstream catalyst and a downstream catalyst.

A full range air-fuel ratio (LAF) sensor 16 is provided upstream of the catalyst converter 15. The LAF sensor 16 linearly detects the concentration of oxygen included in exhaust gas over a wide air-fuel ratio zone, from the rich zone where the air/fuel ratio is richer than the stoichiometric air/fuel ratio to an extremely lean zone. The detected oxygen concentration is sent to the ECU 5.

An O2 (exhaust gas) sensor 17 is provided between the upstream catalyst and the downstream catalyst. The O2 sensor 17 is a binary-type of exhaust gas concentration sensor. The O2 sensor outputs a high level signal when the air-fuel ratio is richer than the stoichiometric air-fuel ratio, and outputs a low level signal when the air-fuel ratio is leaner than the stoichiometric air-fuel ratio. The electric signal is sent to the ECU 5.

A vehicle speed (VP) sensor 23 for detecting vehicle speed is connected to the ECU 5. The detected vehicle speed signal is sent to the ECU 5.

Signals sent to the ECU 5 are passed to the input circuit 5a. The input interface 5a converts analog signal values into digital signal values. The CPU 5b processes the resulting digital signals, performs operations in accordance with the programs stored in the ROM, and creates control signals. The output interface 5d sends these control signals to actuators for a bypass valve 22, fuel injection valve 6 and other mechanical components.

FIG. 2(a) shows a structure of the catalyst converter 15. Exhaust gas introduced into the exhaust manifold 14 passes through the upstream catalyst 25 and then through the downstream catalyst 26. It is known that it is easier to maintain the purification rate of Nox at an optimal level by air-fuel ratio control based on the output of an O2 sensor provided between the upstream and downstream catalysts, compared with air-fuel ratio control based on the output of an O2 sensor provided downstream of the downstream catalyst. Therefore, in the embodiment of the invention, the O2 sensor 17 is provided between the upstream and downstream catalysts. The O2 sensor 17 detects the concentration of oxygen included in exhaust gas after the passage through the upstream catalyst 25.

FIG. 2(b) is a block diagram showing a system from a LAF sensor 16 to the O2 sensor 17 shown in FIG. 2(a). The LAF sensor 16 detects an air-fuel ratio Kact of the exhaust gas supplied to the upstream catalyst 25. The O2 sensor 17 outputs a voltage Vout representing the oxygen concentration of the exhaust gas after the purification by the upstream catalyst 25.

The upstream catalyst 25 and the O2 sensor 17 are disposed in series. There exist delay and dead time of the upstream catalyst 25 and the O2 sensor 17 between an input of the system or the air-fuel ratio Kact and an output of the system or the output Vout of the O2 sensor 17.

Figure 3:
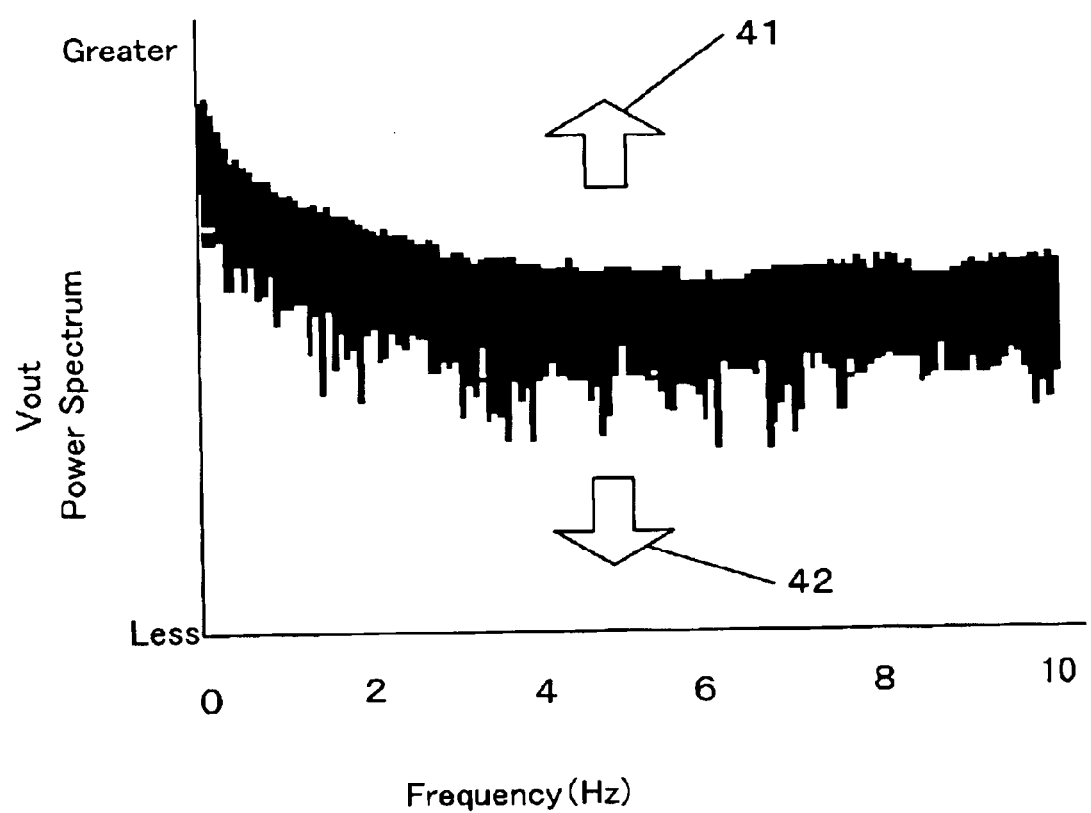
FIG. 3 shows one example of a frequency response of an output of an exhaust gas sensor.

FIG. 3 shows a result of Fourier transformation of the O2 sensor output Vout. If deterioration of the catalyst proceeds, the power spectrum of the sensor output Vout increases in the direction shown by an arrow 41. On the other hand, if the catalyst is a newer one, the power spectrum of the sensor output Vout decreases in the direction shown by an arrow 42. Based on this characteristic, deterioration of the catalyst can be determined.

If the O2 sensor deteriorates, a response delay of the O2 sensor increases. When the response delay increases, the power spectrum of the sensor output Vout decreases in the direction shown by the arrow 42.

Thus, when the O2 sensor deteriorates or is faulty, deterioration of the catalyst cannot be precisely detected since the power spectrum of the sensor output Vout decreases. In other words, a state in which the catalyst is new and a state in which the O2 sensor deteriorates cannot be distinguished by the power spectrum of the sensor output Vout.

Distinguishment of Deterioration of Catalyst from Failure of O2 Sensor

For the sake of easier understanding of the present invention, the scheme of distinguishing deterioration of the catalyst from a failure of the O2 sensor will be described. First, referring to FIGS. 4 and 5, the scheme of detecting deterioration of the catalyst will be described.

Figure 4:
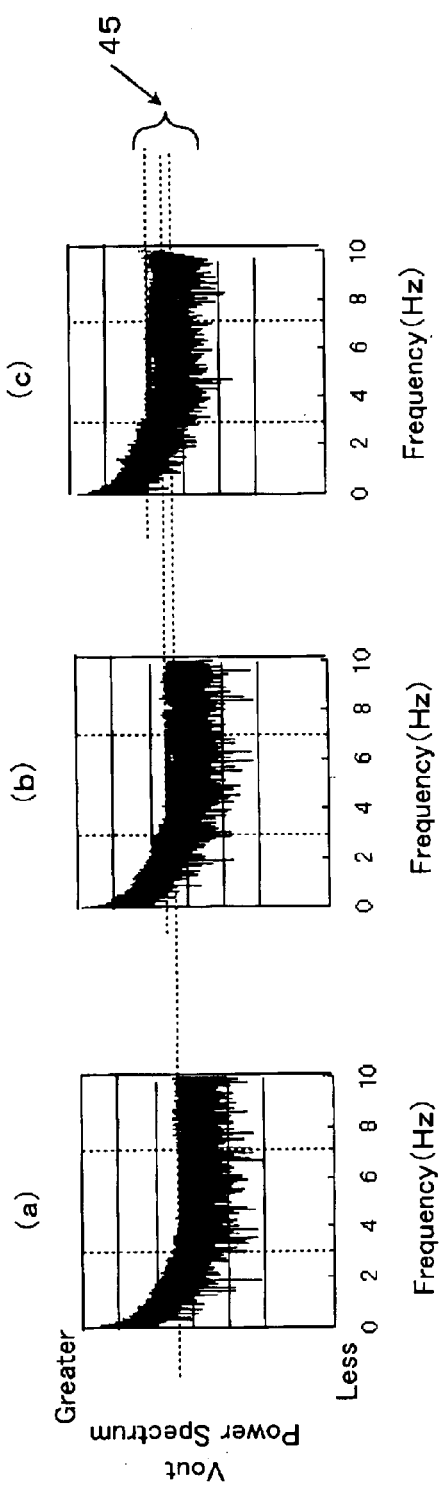
FIG. 4 shows that a frequency response of an output of an exhaust gas sensor varies according to the degree of deterioration of catalyst.
Figure 5:
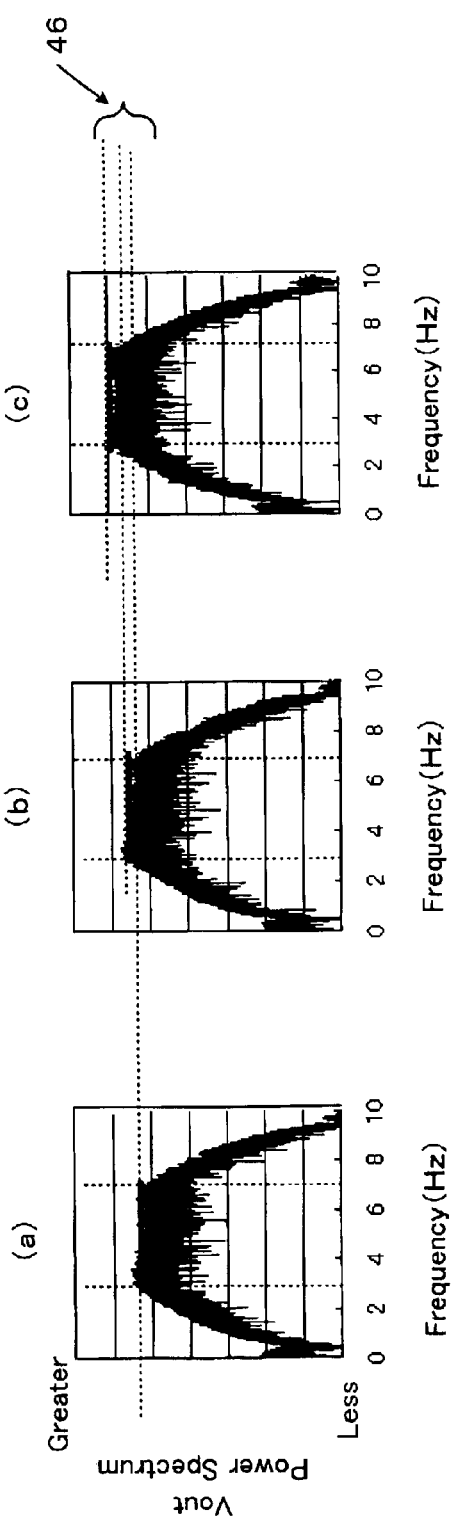
FIG. 5 shows that a frequency response of a filtered output of an exhaust gas sensor varies according to the the degree of deterioration of catalyst.

FIG. 4 shows a power spectrum of the O2 sensor output Vout (a) when the catalyst is new, (b) when the purification rate of the catalyst is sufficient, and (c) when the purification rate of the catalyst is insufficient. In FIGS. 4(a) to 4(c), the level of the power spectrum of the sensor output Vout in the frequency region of 3 through 7 Hz varies, which is indicated by the reference number 45.

FIGS. 5(a) to 5(c) show a result of filtering the sensor output Vout shown in FIGS. 4(a) to 4(c) with a band-pass filter, respectively. The power spectrum of the sensor output Vout in the frequency region of 3 through 7 Hz is emphasized by the filter. As shown by the reference number 46, as the catalyst deteriorates, the power spectrum of the sensor output Vout in the frequency regions 3 to 7 Hz increases. Thus, by evaluating the sensor output Vout in the frequency region of 3 to 7 Hz, it can be determined whether the catalyst is in a deteriorated state.

The scheme of detecting a failure of the O2 sensor will be described. FIG. 6(a) shows one example of variations in the air-fuel ratio Kact, which is detected by the LAF sensor. FIG. 6(b) shows the output of the O2 sensor according to the variations of the air-fuel ratio Kact shown in FIG. 6(a). The reference number 51 indicates the output Vout from a normal O2 sensor. The reference number 52 indicates the output Vout from a faulty O2 sensor.

It is seen that there is a difference between the normal O2 sensor and the faulty O2 sensor in the sensor output Vout corresponding to variations of the air-fuel ratio Kact. Referring to the period from 50 to 80, when a low-frequency variation of large amplitude occurs in the air-fuel ratio Kact, a significant difference appears between the output of the normal O2 sensor and the output of the faulty O2 sensor. The output amplitude of the normal O2 sensor is larger than the output amplitude of the faulty O2 sensor. Thus, a failure of the O2 sensor can be detected based on amplitude of the O2 sensor output when a low-frequency variation of large amplitude occurs in the air-fuel ratio.

In order to emphatically extract a large low-frequency variation in the air-fuel ratio Kact, and to extract the output of the O2 sensor corresponding to the large low-frequency variation of the air-fuel ratio as shown in FIGS. 6(a) and 6(b), a filtering process by a band-pass filter is applied to the air-fuel ratio Kact and the sensor output Vout. FIGS. 7(a) and 7(b) show one example of characteristics of the band-pass filter used for the air-fuel ratio Kact. FIGS. 7(c) and 7(d) show one example of characteristics of the band-pass filter used for the sensor output Vout.

The filter for the air-fuel ratio is designed to extract frequency components of 0.05 through 1.0 (Hz). The filter for the sensor output Vout is designed to extract frequency components of 0.1 through 1.0 Hz. In the embodiment, in order to more precisely detect a failure of the O2 sensor, filters to which the air-fuel ratio Kact and the sensor output Vout are subjected have different characteristics.

Figure 6:
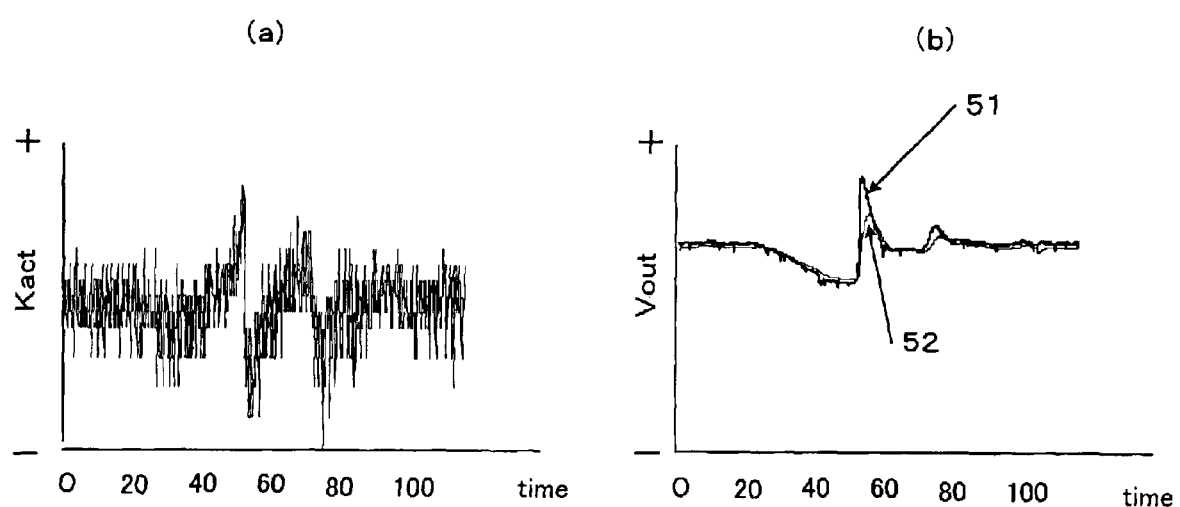
FIG. 6 shows a state in which an output of a normal/abnormal exhaust gas sensor varies according to variations of the air-fuel ratio.
Figure 8:
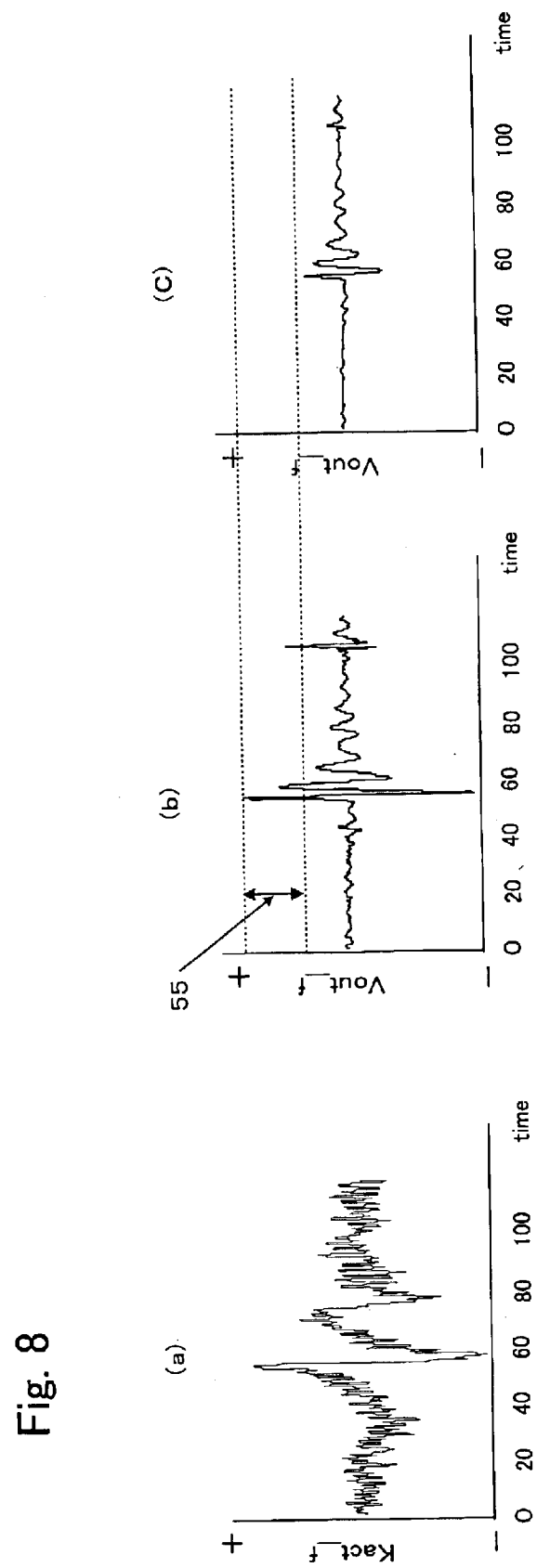
FIG. 8 shows a result of filtering the an air-fuel ratio sensor output and the exhaust gas sensor output shown in FIG. 6 in accordance with one embodiment of the present invention.

FIG. 8(a) shows a filtered air-fuel ratio Kact_f obtained by filtering the air-fuel ratio shown in FIG. 6(a). FIG. 8(b) shows a filtered sensor output Vout_f obtained by filtering the sensor output 51 when the O2 sensor shown in FIG. 6(b) is normal. FIG. 8(c) shows a filtered sensor output Vout_f obtained by filtering the sensor output 52 when the O2 sensor shown in FIG. 6(b) is faulty. As seen compared with FIG. 6, the filtering process enables a correlation between variations in the air-fuel ratio Kact_f and variations in the sensor output Vout_f to clearly appear. An amplitude difference 55 between the output of the normal O2 sensor and the output of the faulty O2 sensor is significantly extracted when a large low-frequency variation occurs in the air-fuel ratio Kact_f. By evaluating the amplitude difference 55, it can be determined whether the O2 sensor is normal or faulty.

Figure 9:
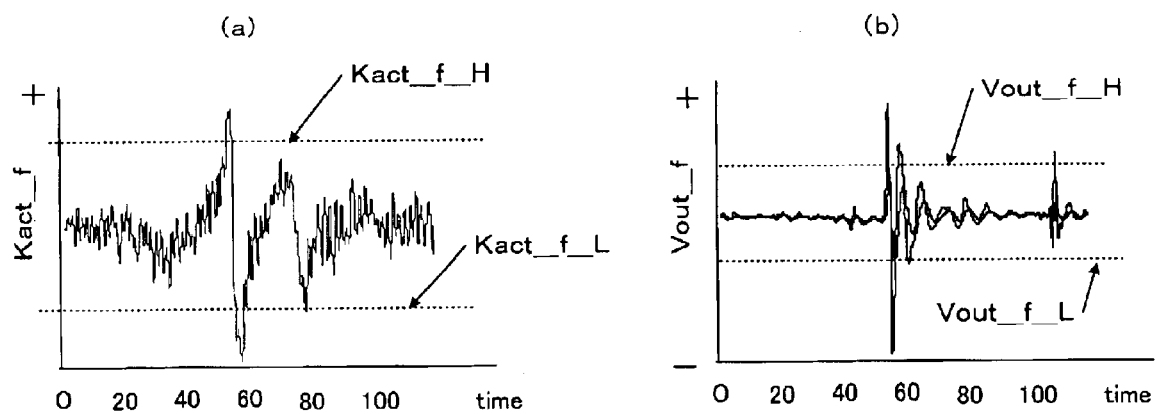
FIG. 9 shows threshold values for a filtered air-fuel ratio and a filtered exhaust gas sensor output in accordance with one embodiment of the present invention.

FIG. 9 shows threshold values that are established so as to extract a large low-frequency variation in the air-fuel ratio, and to extract the sensor output amplitude difference corresponding to the low-frequency variation. As shown in FIG. 9(a), an upper limit value Kact_f_H and a lower limit value Kact_f_L are set for the filtered air-fuel ratio Kact_f. As shown in FIG. 9(b), an upper limit value Vout_f_H and a lower limit value Vout_f_L are set for the sensor output Vout.

Figure 10:
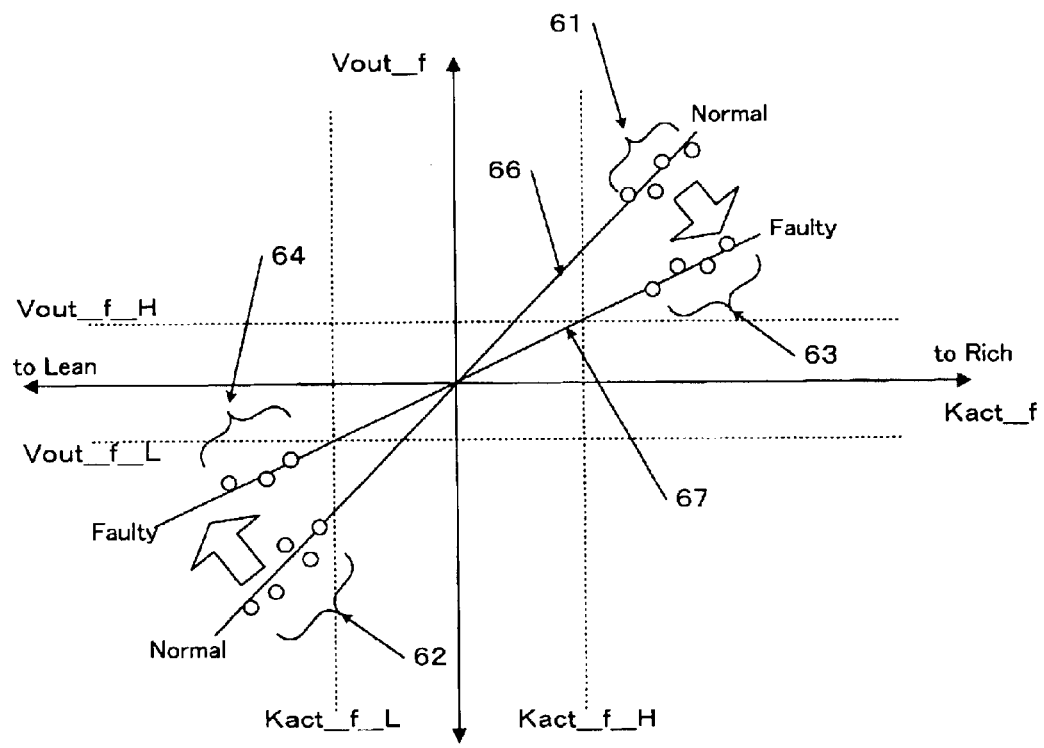
FIG. 10 shows a correlation between an air-fuel ratio and an exhaust gas sensor output when the exhaust gas sensor is normal and a correlation between an air-fuel ratio and an exhaust gas sensor output when the exhaust gas sensor is faulty in accordance with one embodiment of the present invention.

FIG. 10 shows a correlation between the filtered air-fuel ratio Kact_f and the sensor output Vout_f. A region in which the filtered air-fuel ratio Kact_f is greater than zero is a rich region. A region in which the air-fuel ratio Kact_f is less than zero is a lean region.

Each of points 61 shows a filtered sensor output Vout_f that is plotted corresponding to the filtered air-fuel ratio Kact_f that exceeds the upper limit value Kact_f_H when the O2 sensor is normal. Each of points 62 shows a filtered sensor output Vout_f that is plotted corresponding to the filtered air-fuel ratio Kact_f that is lower than the lower limit value Kact_f_L when the O2 sensor is normal. Each of points 63 shows a filtered sensor output Vout_f that is plotted corresponding to the filtered air-fuel ratio Kact_f that exceeds the upper limit value Kact_f_H when the O2 sensor is faulty. Each of points 64 shows a filtered sensor output Vout_f that is plotted corresponding to the air-fuel ratio Kact_f that is lower than the lower limit value Kact_f_L when the O2 sensor is faulty.

A straight line 66 can be drawn based on the plotted points 61 and 62. A straight line 67 can be drawn based on the plotted points 63 and 64. Each of the straight lines 66 and 67 represents a correlation function between the filtered air-fuel ratio Kact_f and the filtered sensor output Vout_f. A slope of the correlation function represents a ratio between the amount of variations in the air-fuel ratio Kact_f and the amount of variations in the sensor output Vout_f. The slope varies according to whether the O2 sensor is normal or faulty. A failure of the O2 sensor can be detected based on the slope of the correlation function.

The correlation functions for the rich region and the lean region are expressed in the following equations (1) and (2), respectively. Ao2r and Ao2l indicate the slope of the correlation function in the rich region and the slope of the correlation function in the lean region, respectively. Ao2r and Ao2l are referred to as a rich correlation coefficient and a lean correlation coefficient, respectively. "d" indicates a dead time in both the upstream catalyst and the O2 sensor. "k" indicates an identifier for identifying a control cycle. Based on the calculated correlation coefficients Ao2r and Ao2l, it is determined whether the O2 sensor is normal or faulty.

$$\text{Vout}\_f(k) = Ao2r \cdot \text{Kact}\_f(k-d) \quad (1)$$

$$\text{Vout}\_f(k) = Ao2l \cdot \text{Kact}\_f(k-d) \quad (2)$$

As described above, since deterioration of the catalyst affects the O2 sensor output in the frequency region mainly from 3 to 7 Hz, the deterioration of the catalyst can be detected by evaluating the sensor output Vout in this frequency region. On the other hand, deterioration of the O2 sensor can be detected by comparing the air-fuel ratio sensor output Kact with the O2 sensor output Vout when a large variation of the air-fuel ratio occurs in a frequency region that is lower than the frequency region used for the deterioration detection for the catalyst. Since the frequency region used for the failure detection for the O2 sensor is different from the frequency region used for the deterioration detection for the catalyst, it is possible to clearly distinguish deterioration of the catalyst from a failure of the O2 sensor.

Structure of Failure Detection Apparatus

Figure 7:
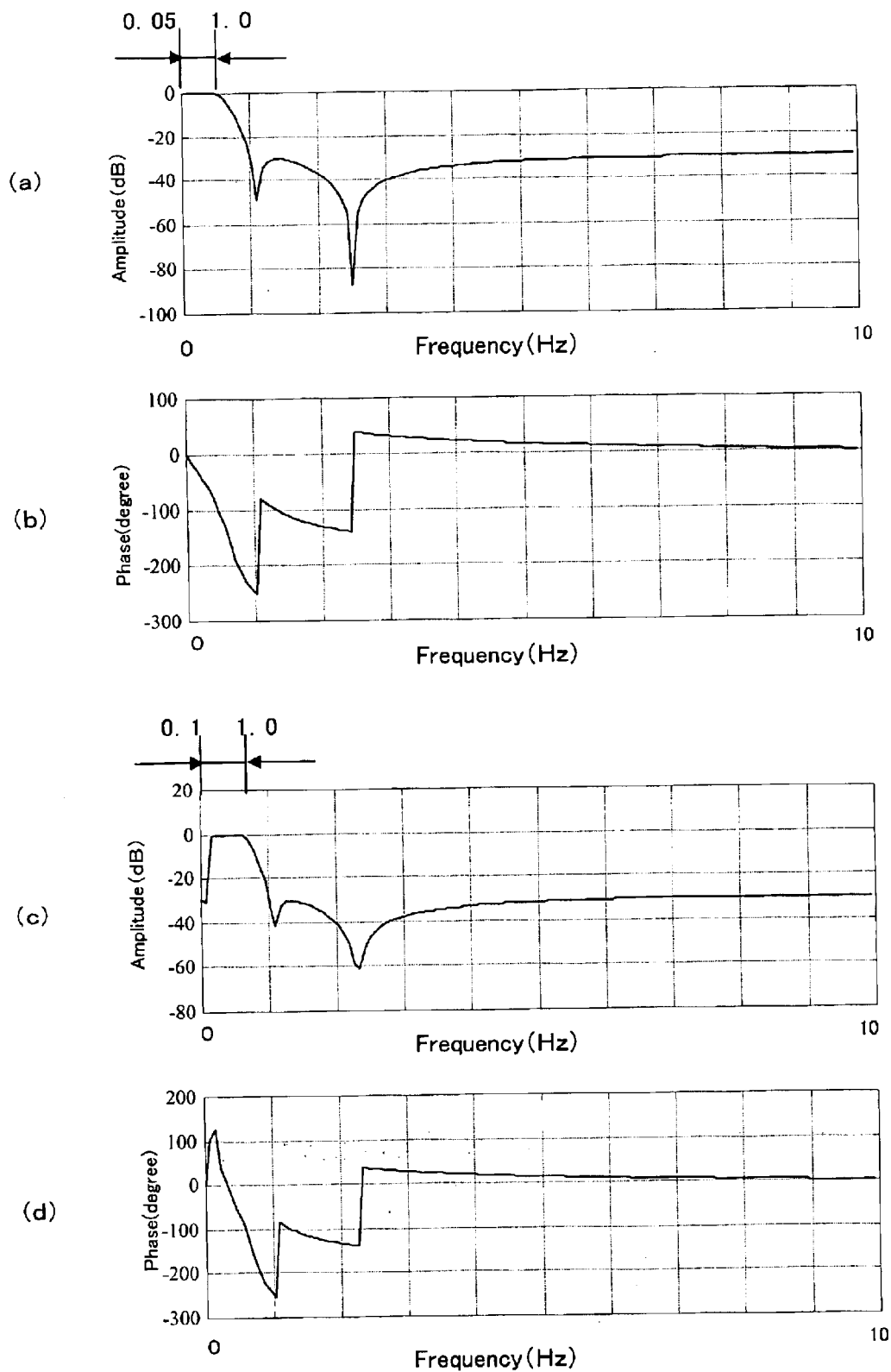
FIG. 7 shows filter characteristics of a band-pass filter in accordance with one embodiment of the present invention.

FIG. 11 is a functional block diagram of an apparatus for detecting a failure of the O2 sensor according to one embodiment of the present invention. The air-fuel ratio Kact and the sensor output Vout respectively detected by the LAF sensor 16 and the O2 sensor 17 are applied to band-pass filters having filter characteristics as shown in FIG. 7. A first band-pass filter 71 filters the air-fuel ratio Kact in accordance with the equation (3). A second band-pass filter 72 filters the sensor output Vout in accordance with the equation (4). Here, ak1, ka2, . . . , akn, bk0, bk1, . . . , bkm, and av1, av2, . . . , avn, bv0, bv1, . . . , bvm are filter coefficients that are predetermined by simulation or the like.

$$\text{Kact\_f}(k) = ak1 \cdot \text{Kact\_f}(k-1) + ak2 \cdot \text{Kact\_f}(k-2) +, \ldots, + \quad (3)$$
$$akn \cdot \text{Kact\_f}(k-n) + bk0 \cdot \text{Kact}(k) + bk1 \cdot$$
$$\text{Kact}(k-1) +, \ldots, + bkm \cdot \text{Kact}(k-m)$$

$$\text{Vout\_f}(k) = av1 \cdot \text{Vout\_f}(k-1) + av2 \cdot \text{Vout\_f}(k-2) +, \ldots, + \quad (4)$$
$$avn \cdot \text{Vout\_f}(k-n) + bv0 \cdot \text{Vout}(k) + bv1 \cdot$$
$$\text{Vout}(k-1) +, \ldots, + bvm \cdot \text{Vout}(k-m)$$

In the embodiment, filters having different transmission characteristics are used for the air-fuel ratio Kact and the sensor output Vout as described referring to FIG. 7. Alternatively, filters having the same transmission characteristics may be used. A low pass filter may be also used instead of the band-pass filter. Since a band-pass filter capable of passing low frequency components tends to be unstable, a high pass filter and a low pass filter may be applied serially.

A first sampling section 73 compares the filtered air-fuel ratio Kact_f with the upper limit value Kact_f_H to sample an air-fuel ratio Kact_f that exceeds the upper limit value Kact_f_H. This sample is referred to as a rich-side sample. Similarly, the first sampling section 73 compares the filtered air-fuel ratio Kact_f with the lower limit value Kact_f_L to sample an air-fuel ratio Kact_f that is lower than the lower limit value Kact_f_L. This sample is referred to as a lean-side sample. A second sampling section 74 samples a sensor output Vout_f corresponding to the air-fuel ratio Kact_f sampled by the first sampling section 73.

A first peak processing section 75 extracts a sample having the maximum absolute value from the rich-side samples Kact_f that are sampled by the first sampling section 73 and then holds it as a peak value (peak holding process). The first peak processing section 75 uses the peak value as a reference to extract samples in the vicinity of the peak value.

Similarly, the first peak processing section 75 extracts a sample having the maximum absolute value from the lean-side samples Kact_f that are sampled by the first sampling section 73, and holds it as a peak value (peak holding process). The first peak processing section 75 uses the peak value as a reference to extract samples in the vicinity of the peak value.

A second peak processing section 76 extracts a sample having the maximum absolute value from the rich-side samples Vout_f that are sampled by the second sampling section 74, and holds it as a peak value (peak holding process). The second peak processing section 76 uses the peak value as a reference to extract samples in the vicinity of the peak value.

Similarly, the second peak processing section 76 extracts a sample having the maximum absolute value from the lean-side samples Vout_f that are sampled by the second sampling section 74, and holds it as a peak value (peak holding process). The second peak processing section 76 uses the held peak value as a reference to extract samples in the vicinity of the peak value.

Figure 12:
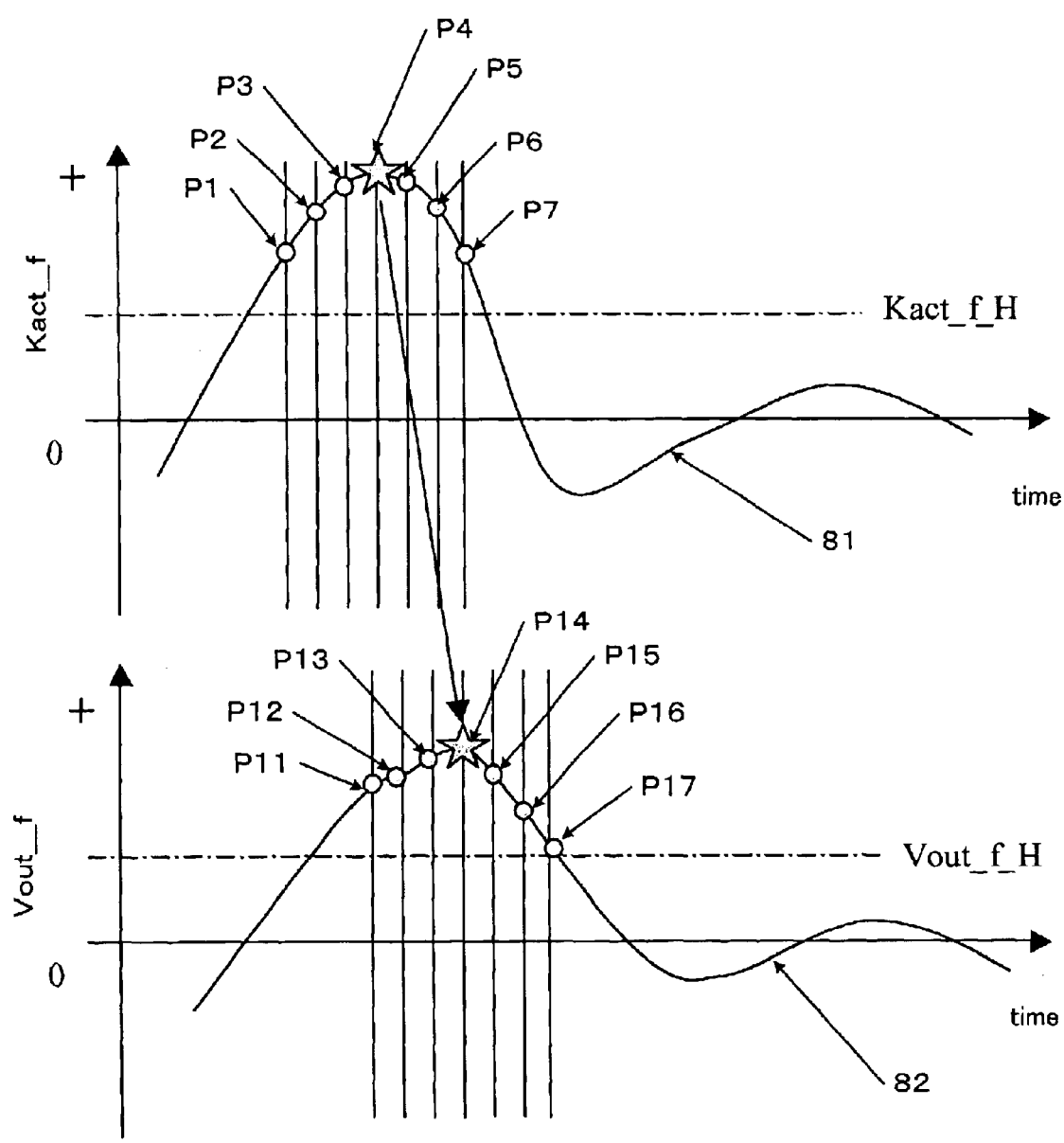
FIG. 12 shows samples extracted in peak holding processes for an air-fuel ratio and an exhaust gas sensor output in accordance with one embodiment of the present invention.

Now referring to FIG. 12, the peak holding process will be described. A curve 81 shows one example of the filtered air-fuel ratio Kact_f in the rich region. A curve 82 shows one example of the filtered sensor output Vout_f in the rich region.

Samples P1 through P7 exceeding the upper limit value Kact_f_H are sampled by the first sampling section 73. From the samples P1 through P7, the first peak processing section 75 holds the sample P4 having the maximum amplitude as a peak value Kact_f_peakr. The first peak processing section 75 extracts three samples P1, P2 and P3 on the left side of the sample P4 and three samples P5, P6 and P7 on the right side of the sample P4.

A similar process is carried out for the sensor output Vout. Samples P11 through P17 corresponding to the samples P1 through P7 are sampled by the second sampling section 74. From the samples P11 through P17, the sample P14 is held as a peak value Vout_f_peakr. Three samples P11, P12 and P13 on the left side of the sample P14 and three samples P15, P16 and P17 on the right side of the sample P14 are extracted.

By carrying out the peak holding process, the correlation between the filtered air-fuel ratio Kact_f and the filtered sensor output Vout_f is enhanced. That is, by associating the peak value of the air-fuel ratio Kact_f with the peak value of the sensor output Vout_f, other samples of Kact_f are appropriately associated in time with other samples of Vout_f. Thus, (P1, P11), (P2, P12), (P3, P13), (P5, P15), (P6, P16), and (P7, P17) are generated with respect to a pair of the peak values (P4, P14). By enhancing the correlation of the air-fuel ratio and the sensor output, the correlation coefficients can be determined with more accuracy.

Referring back to FIG. 11, a statistical processing section 77 applies a successive least squares method to the extracted samples to calculate the correlation coefficients Ao2r and Ao2l. In the equations (5) to (8), the rich-side correlation coefficient Ao2r is calculated by applying the successive least squares method to the extracted rich-side samples.

$$Ao2r(k) = Ao2r(k-1) + KPr(k) \cdot Eo2r(k) \quad (5)$$

An error Eo2r(k) shown in the equation (5) is calculated in accordance with the following equation (6). A gain coefficient KPr(k) is calculated in accordance with the equation (7).

$$Eo2r(k) = \begin{cases} \text{Vout\_f}(k) - Ao2r(k-1) \cdot \text{Kact\_f}(k-d) & (6) \\ \quad \text{if } \text{Vout\_f}(k) \geq \text{Vout\_f\_H} \\ \quad \text{and } \text{Kact\_f}(k) \geq \text{Kact\_f\_H} \\ 0 \quad \text{if } \text{Vout\_f}(k) < \text{Vout\_f\_H} \\ \quad \text{or } \text{Kact\_f}(k) < \text{Kact\_f\_H} \end{cases}$$

$$KPr(k) = \frac{Pr(k) \cdot \text{Kact\_f}(k-d)}{1 + Pr(k) \cdot \text{Kact\_f}(k-d)^2} \quad (7)$$

"Pr" in the equation (7) is calculated in accordance with the equation (8).

$$Pr(k+1) = \begin{cases} \frac{1}{\lambda_1}\left(1 - \frac{\lambda_2 \cdot Pr(k) \cdot \text{Kact\_f}(k-d)}{\lambda_1 + \lambda_2 \cdot Pr(k) \cdot \text{Kact\_f}(k-d)^2}\right) \cdot Pr(k) \\ \quad \text{if Vout\_f}(k) \geq \text{Vout\_f\_H} \\ \quad \text{and Kact\_f}(k) \geq \text{Kact\_f\_H} \\ Pr(k) \quad \text{if Vout\_f}(k) < \text{Vout\_f\_H} \\ \quad \text{or Kact\_f}(k) < \text{Kact\_f\_H} \end{cases} \quad (8)$$

Similarly, the lean-side correlation coefficient Ao2l is calculated by applying the successive least squares method to the extracted lean-side samples in accordance with the equations (9) to (12).

$$Ao2l(k) = Ao2l(k-1) + KPl(k) \cdot Eo2l(k) \quad (9)$$

An error Eo2l(k) shown in the equation (9) is calculated in accordance with the equation (10). A gain coefficient KPl(k) is calculated in accordance with the equation (11).

$$Eo2l(k) = \begin{cases} \text{Vout\_f}(k) - Ao2l(k-1) \cdot \text{Kact\_f}(k-d) \\ \quad \text{if Vout\_f}(k) \leq \text{Vout\_f\_L} \\ \quad \text{and Kact\_f}(k) \leq \text{Kact\_f\_L} \\ 0 \quad \text{if Vout\_f}(k) > \text{Vout\_f\_L} \\ \quad \text{or Kact\_f}(k) > \text{Kact\_f\_L} \end{cases} \quad (10)$$

$$KPl(k) = \frac{Pl(k) \cdot \text{Kact\_f}(k-d)}{1 + Pl(k) \cdot \text{Kact\_f}(k-d)^2} \quad (11)$$

"Pl" in the equation (11) is determined in accordance with the equation (12).

$$Pr(k+1) = \begin{cases} \frac{1}{\lambda_1}\left(1 - \frac{\lambda_2 \cdot Pl(k) \cdot \text{Kact\_f}(k-d)}{\lambda_1 + \lambda_2 \cdot Pl(k) \cdot \text{Kact\_f}(k-d)^2}\right) \cdot Pl(k) \\ \quad \text{if Vout\_f}(k) \leq \text{Vout\_f\_L} \\ \quad \text{and Kact\_f}(k) \leq \text{Kact\_f\_L} \\ Pl(k) \quad \text{if Vout\_f}(k) > \text{Vout\_f\_L} \\ \quad \text{or Kact\_f}(k) > \text{Kact\_f\_L} \end{cases} \quad (12)$$

Variations may occur in the air-fuel ratio sensor output and the O2 sensor output due to noise conditions. These sensor outputs may also vary according to the operating state of the vehicle/engine. The application of the successive least squares method can minimize the influence caused by such variations on the failure detection.

By carrying out the successive least squares method, it is unnecessary to hold the air-fuel ratio Kact_f and the sensor output Vout_f after the statistical process in each cycle, thereby economizing on memory usage.

Alternatively, a non-successive least squares method may be used. The type of least squares method is determined by the values of $\lambda_1$ and $\lambda_2$ in the equation (8). For example, in a fixed gain method, $\lambda_1=1$ and $\lambda_2=0$. In a least-squares method, $\lambda_1=1$ and $\lambda_2=1$. In a decreasing gain method, $\lambda_1=1$ and $\lambda_2=\lambda$. In a weighted least squares method, $\lambda_1=\lambda$ and $\lambda_2=1$.

A failure determination section 78 determines whether the O2 sensor is normal or faulty based on the correlation coefficients obtained by the statistical processing section 77. In the rich region, if the correlation coefficient Ao2r is less than a predetermined value Ao2r_BR, it is determined that the O2 sensor is faulty. If the correlation coefficient Ao2r is equal to or greater than the predetermined value Ao2r_BR, it is determined that the O2 sensor is normal.

Similarly, if the correlation coefficient Ao2l is less than a predetermined value Ao2l_BR, the failure determination section 78 determines that the O2 sensor is faulty. If the correlation coefficient Ao2l is equal to or greater than the predetermined value Ao2l_BR, the failure determination section 78 determines that the O2 sensor is normal.

If it is determined that the O2 sensor is normal, a flag F_O2BR is set to zero. If it is determined that the O2 sensor is faulty, the flag F_O2BR is set to one. When the value of the flag F_O2BR is one, an MIL (warning light) may be lit to inform a passenger that the O2 sensor is faulty.

In another embodiment, if the flag F_O2BR is set to one either in the rich region or in the lean region, the failure determination section 78 determines that the O2 sensor is faulty. Alternatively, the correlation coefficient of either the rich region or the lean region may be calculated to determine whether the O2 sensor is normal or faulty.

FIG. 13 is a functional block diagram of an apparatus for detecting a failure of the O2 sensor in accordance with a second embodiment of the present invention. In the first embodiment, the slope of the correlation function shown in FIG. 10 is subjected to the statistical process. In the second embodiment, the filtered air-fuel ratio Kact_f and the filtered sensor output Vout_f are subjected to the statistical process. The slope of the correlation function is calculated based on the statistically processed air-fuel ratio Kact_f and sensor output Vout_f.

The first and second band-pass filters 71 and 72, the first and second sampling sections 73 and 74, and the first and second peak processing sections 75 and 76 operate in a similar way to those in the first embodiment.

A first statistical processing section 91 applies the successive least squares method to the rich-side samples Kact_f, which are extracted by the first peak processing section 75, in accordance with the equations (13) through (16) to determine a statistically processed sample Kact_f_LSH in the rich region.

$$\text{Kact\_f\_LSH}(k) = \text{Kact\_f\_LSH}(k-1) + KPkah(k) \cdot Ekah(k) \quad (13)$$

An error Ekah(k) is calculated in accordance with the equation (14). A gain coefficient KPkah(k) is calculated in accordance with the equation (15).

$$Ekah(k) = \begin{cases} \text{Kact\_f}(k) - \text{Kact\_f\_LSH}(k-1) \\ \quad \text{if Kact\_f}(k) \geq \text{Kact\_f\_H} \\ 0 \quad \text{if Kact\_f}(k) < \text{Kact\_f\_H} \end{cases} \quad (14)$$

$$KPkah(k) = \frac{Pkah(k)}{1 + Pkah(k)} \quad (15)$$

"Pkah" in the equation (15) is determined in accordance with the equation (16).

$$Pkah(k+1) = \begin{cases} \frac{1}{\lambda_1}\left(1 - \frac{\lambda_2 \cdot Pkah(k)}{\lambda_1 + \lambda_2 \cdot Pkah(k)}\right) \cdot Pkah(h) \\ \quad \text{if Kact\_f}(k) \geq \text{Kact\_f\_H} \\ Pkah(k) \quad \text{if Kact\_f}(k) < \text{Kact\_f\_H} \end{cases} \quad (16)$$

Similarly, the first statistical processing section 91 applies the successive least squares method to the lean-side samples Kact_f, which are extracted by the first peak processing section 75, in accordance with the equations (17) through (20) to determine a statistically processed sample Kact_f_LSL in the lean region.

$$\text{Kact\_f\_LSL}(k) = \text{Kact\_f\_LSL}(k-1) + KPkal(k) \cdot Ekal(k) \quad (17)$$

An error Ekal(k) shown in the equation (17) is calculated in accordance with the equation (18). A gain coefficient KPkal(k) is calculated in accordance with the equation (19).

$$Ekal(k) = \begin{cases} Kact\_f(k) - Kact\_f\_LSL(k-1) \\ \quad \text{if } Kact\_f(k) \leq Kact\_f\_L \\ 0 \quad \text{if } Kact\_f(k) > Kact\_f\_L \end{cases} \quad (18)$$

$$KPkal(k) = \frac{Pkal(k)}{1 + Pkal(k)} \quad (19)$$

"Pkal" in the equation (19) is determined in accordance with the equation (20).

$$Pkal(k+1) = \begin{cases} \frac{1}{\lambda_1}\left(1 - \frac{\lambda_2 \cdot Pkal(k)}{\lambda_1 + \lambda_2 \cdot Pkal(k)}\right) \cdot Pkal(k) \\ \quad \text{if } Kact\_f(k) \leq Kact\_f\_L \\ Pkal(k) \quad \text{if } Kact\_f(k) > Kact\_f\_L \end{cases} \quad (20)$$

A second statistical processing section 92 applies the successive least squares method to the rich-side samples Vout_f, which are extracted by the second peak processing section 76, in accordance with the equations (21) through (24) to determine a statistically processed sample Vout_f_LSH in the rich region.

$$Vout\_f\_LSH(k) = Vout\_f\_LSH(k-1) + KPo2h(k) \cdot Eo2h(k) \quad (21)$$

An error Eo2h(k) shown in the equation (21) is calculated in accordance with the equation (22). A gain coefficient KPo2h(k) is calculated in accordance with the equation (23).

$$Eo2h(k) = \begin{cases} Vout\_f(k) - Vout\_f\_LSH(k-1) \\ \quad \text{if } Vout\_f(k) \geq Vout\_f\_H \\ 0 \quad \text{if } Vout\_f(k) < Vout\_f\_H \end{cases} \quad (22)$$

$$KPo2h(k) = \frac{Po2h(k)}{1 + Po2h(k)} \quad (23)$$

"Pko2h" in the equation (23) is determined in accordance with the equation (24).

$$Po2h(k+1) = \begin{cases} \frac{1}{\lambda_1}\left(1 - \frac{\lambda_2 \cdot Po2h(k)}{\lambda_1 + \lambda_2 \cdot Po2h(k)}\right) \cdot Po2h(h) \\ \quad \text{if } Vout\_f(k) \geq Vout\_f\_H \\ Po2h(k) \quad \text{if } Vout\_f(k) \geq Vout\_f\_H \end{cases} \quad (24)$$

Similarly, the second statistical processing section 92 applies the successive least squares method to the lean-side samples Vout_f, which are extracted by the second peak processing section 76, in accordance with the equations (25) through (28) to determine a statistically processed sample Vout_f LSL in the lean region.

$$Vout\_f\_LSL(k) = Vout\_f\_LSL(k-1) + KPo2l(k) \cdot Eo2l(k) \quad (25)$$

An error Eo2l(k) in the equation (25) is calculated in accordance with the equation (26). A gain coefficient KPo2l(k) is calculated in accordance with the equation (27).

$$Eo2l(k) = \begin{cases} Vout\_f(k) - Vout\_f\_LSL(k-1) \\ \quad \text{if } Vout\_f(k) \leq Vout\_f\_L \\ 0 \quad \text{if } Vout\_f(k) > Vout\_f\_L \end{cases} \quad (26)$$

$$KPo2l(k) = \frac{Po2l(k)}{1 + Po2l(k)} \quad (27)$$

"Po2l" in the equation (27) is determined in accordance with the equation (28).

$$Po2l(k+1) = \begin{cases} \frac{1}{\lambda_1}\left(1 - \frac{\lambda_2 \cdot Po2l(k)}{\lambda_1 + \lambda_2 \cdot Po2l(k)}\right) \cdot Po2l(h) \\ \quad \text{if } Vout\_f(k) \leq Vout\_f\_L \\ Vout(k) \quad \text{if } Vout\_f(k) \geq Vout\_f\_L \end{cases} \quad (28)$$

A failure determination section 93 determines a ratio between the statistically processed air-fuel ratio Kact_f_LSH and the statistically processed sensor output Vout_f_LSH calculated by the first and second statistical processing sections 91 and 92 for the rich region. If the ratio Vout_f_LSH/Kact_f_LSH is less than the predetermined value Ao2r_BR, it is determined that the O2 sensor is faulty. If the ratio Vout_f_LSH/Kact_f_LSH is equal to or greater than the predetermined value Ao2r_BR, it is determined that the O2 sensor is normal. The predetermined value Ao2r_BR is the same as that used in the first embodiment.

Similarly, the failure determination section 93 determines a ratio between the statistically processed air-fuel ratio Kact_f_LSL and the statistically processed sensor output Vout_f_LSL calculated by the first and second statistical processing sections 91 and 92 for the lean region. If the ratio Vout_f_LSL/Kact_f_LSL is less than the predetermined value Ao2r_BR, it is determined that the O2 sensor is faulty. If the Vout_f_LSL/Kact_f_LSL is equal to or greater than the predetermined value Ao2r_BR, it is determined that the O2 sensor is normal.

If it is determined that the O2 sensor is normal, the flag F_O2BR is set to zero. If it is determined that the O2 sensor is faulty, the flag F_O2BR is set to one.

Flowchart for Detecting a Failure of O2 sensor

Figure 14:
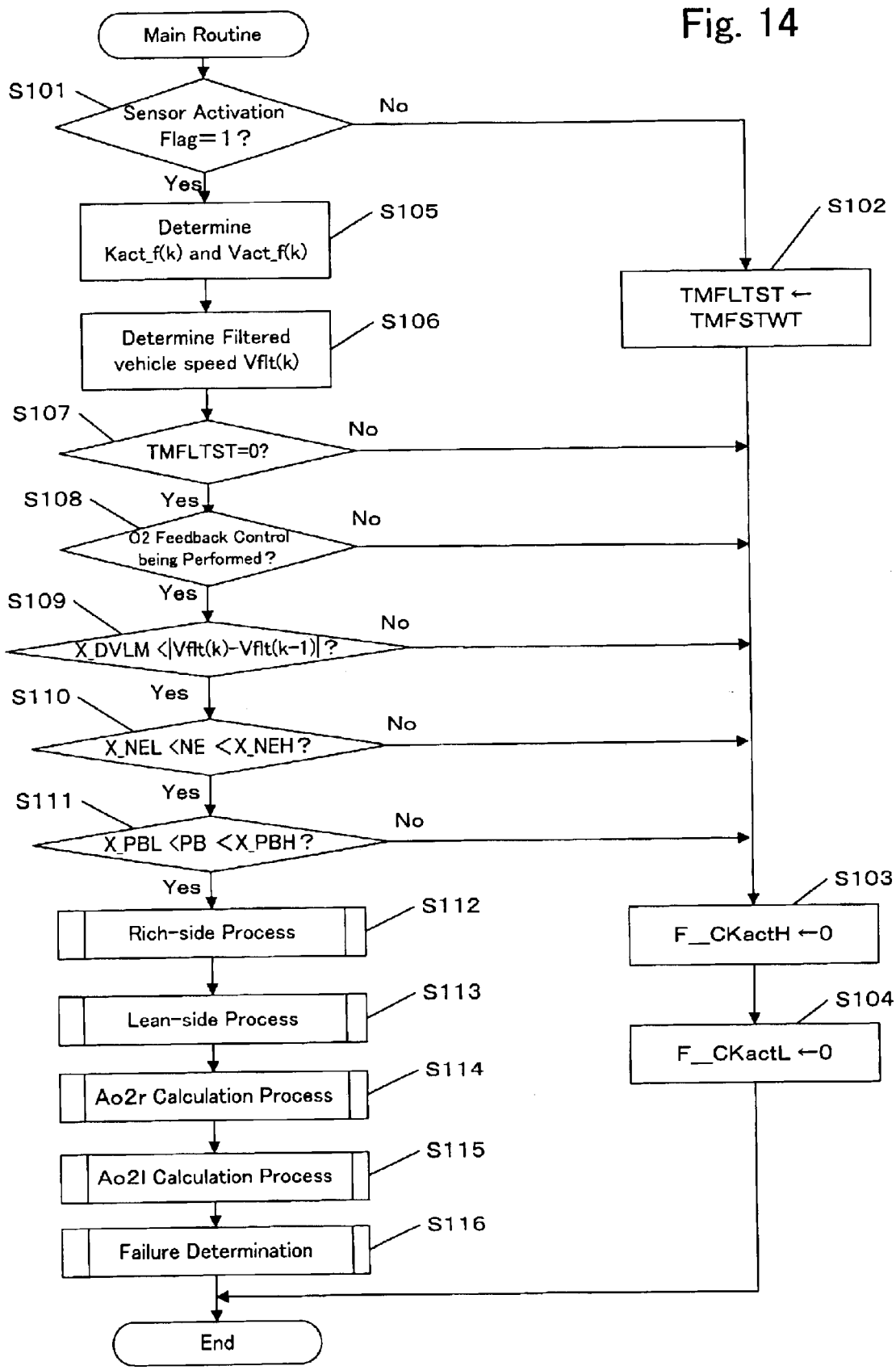
FIG. 14 is a flowchart showing a main routine for a failure detection process in accordance with one embodiment of the present invention.

FIG. 14 shows a main routine for detecting a failure of an O2 sensor in accordance with the first embodiment of the present invention. In step S101, it is determined whether the value of a sensor activation flag is one. The sensor activation flag is a flag that is to be set to one when both the O2 sensor and the air-fuel ratio (LAF) sensor are activated. If the sensor activation flag is zero, a timer TMFLTST is set to a predetermined value TMFSTWT (S102). The predetermined value TMFSTWT is set to time (e.g., 1.0 second) required to stabilize the output of the band-pass filter. In steps S103 and S104, continuation flags F_CKactH and F_CKactL are initialized to zero.

In step S101, if the value of the sensor activation flag is one, the filtering process is applied to the air-fuel ratio Kact and the sensor output Vout in accordance with the above equations (3) and (4) to determine Kact_f(k) and Vout_f(k) (S105). In step S106, in order to determine whether the vehicle is at cruise, a low-pass filtering process is applied to the vehicle speed Vp in accordance with the following equation (29). Thus, a filtered vehicle speed Vflt is determined. Here, afl, . . . , afn and bf0, . . . , bfm are low pass filter coefficients. A Butterworth filter or the like can be used as the low pass filter.

$$Vflt(k) = afl \cdot Vflt(k-1) +, \ldots, + afn \cdot Vflt(k-n) + \\ bf0 \cdot Vp(k) +, \ldots, + bfm \cdot Vp(k-m) \quad (29)$$

In step S107, it is determined whether the timer TMFLTST set in the step S102 indicates zero. If the timer indicates zero, it is determined whether O2 feedback control is being carried out (S108). If the O2 feedback control is being carried out, the process proceeds to step S109. Thus, when the output of the band-pass filter is stabilized and the air-fuel ratio is appropriately controlled by the O2 feedback control, the failure detection process for the O2 sensor is carried out.

In step S109, the filtered vehicle speed Vflt(k) in the current cycle and the filtered vehicle speed Vflt(k−1) in the previous cycle are compared to determine whether a change in the vehicle speed is greater than a predetermined value. If the change in the vehicle speed is greater than the predetermined value X_DVLM, it indicates that the current state is not appropriate for carrying out the failure detection for the O2 sensor, proceeding to step S103. In step S110, it is determined whether the engine rotational speed Ne is within a predetermined range (between a lower limit value X_NEL and an upper limit value X_NEH). If the engine rotational speed Ne is not within the predetermined range, it indicates that the current state is not appropriate for carrying out the failure detection for the O2 sensor, proceeding to step S103. In step S110, it determined whether the intake manifold pressure PB is within a predetermined range (between a lower limit value X_PBL and an upper limit value X_PBH). If the intake manifold pressure PB is not within the predetermined range, it indicates that the current state is not appropriate for carrying out the failure detection for the O2 sensor, proceeding to step S103.

Figure 15:
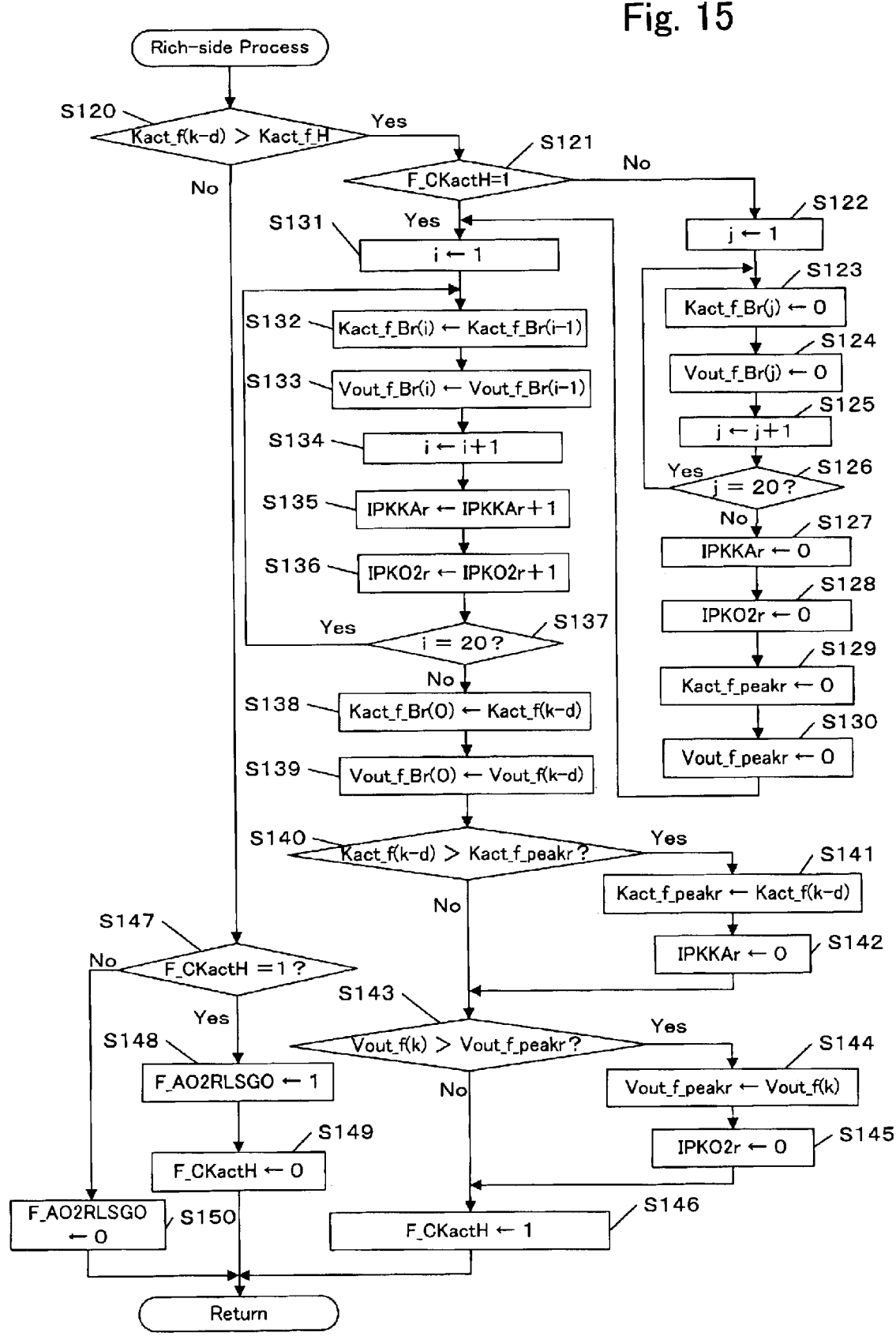
FIG. 15 is a flowchart showing a routine for extracting rich-side samples in accordance with one embodiment of the present invention.
Figure 16:
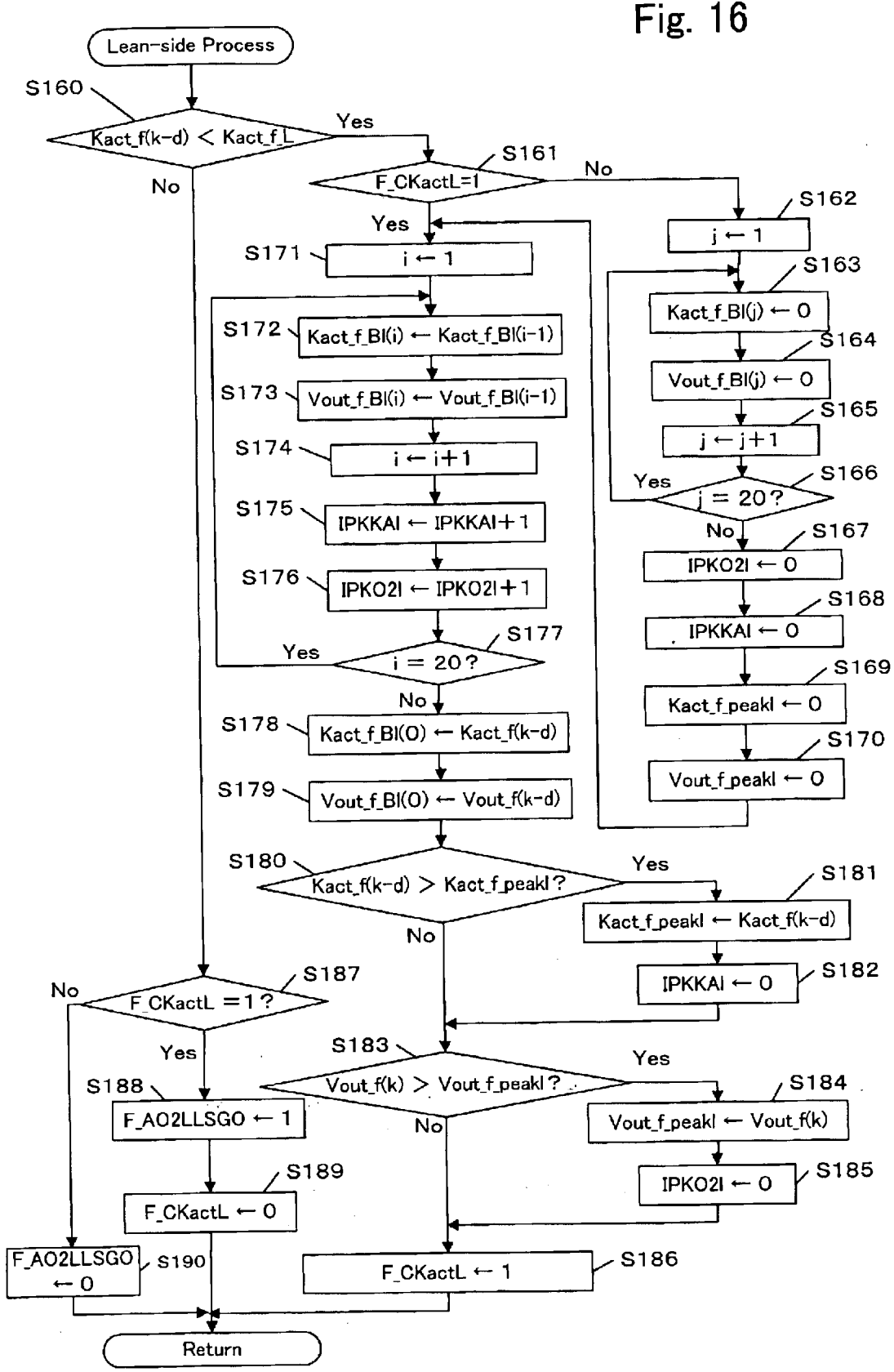
FIG. 16 is a flowchart showing a routine for extracting lean-side samples in accordance with one embodiment of the present invention.
Figure 17:
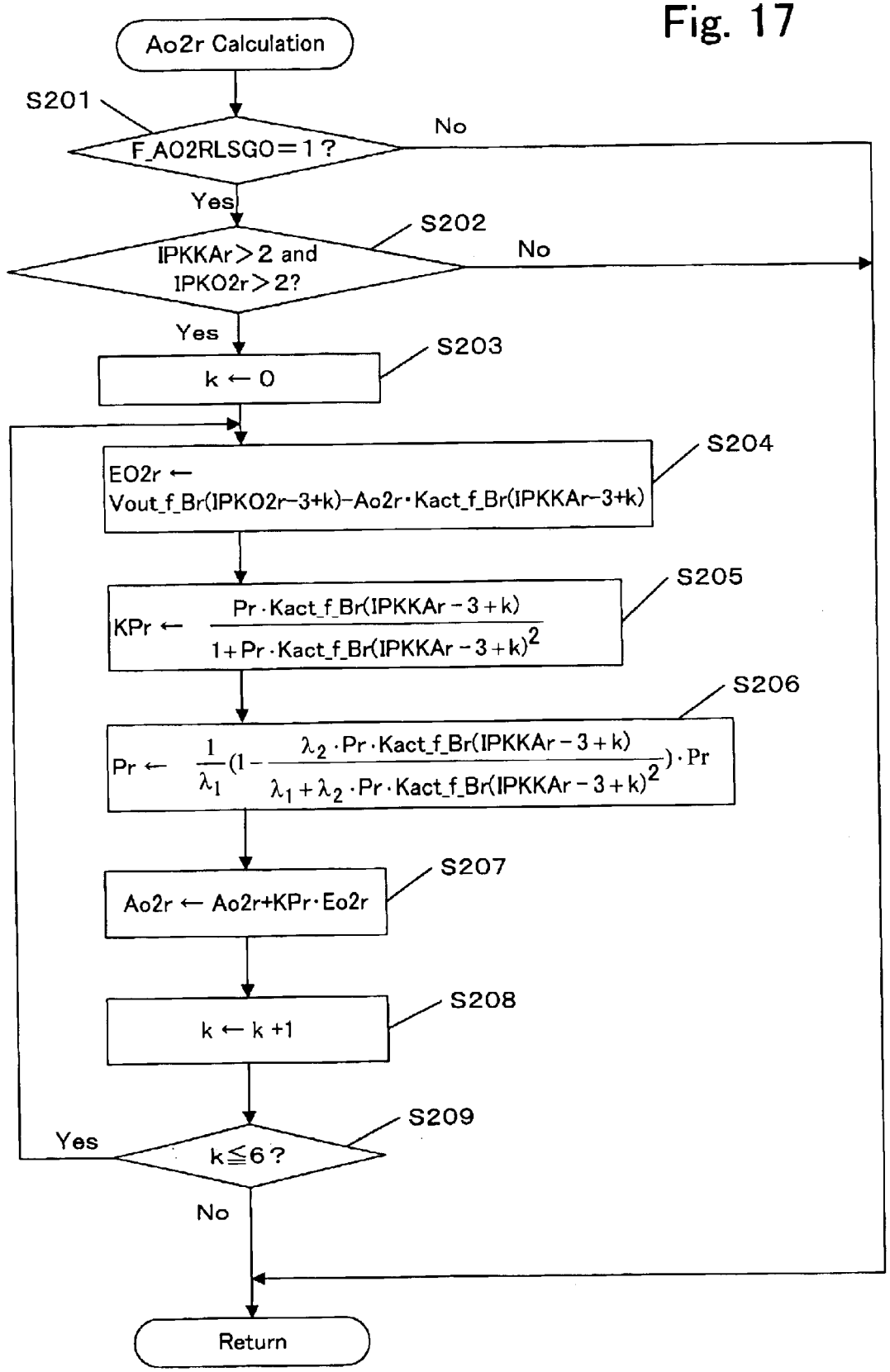
FIG. 17 is a flowchart showing a routine for calculating a rich side correlation coefficient in accordance with one embodiment of the present invention.
Figure 18:
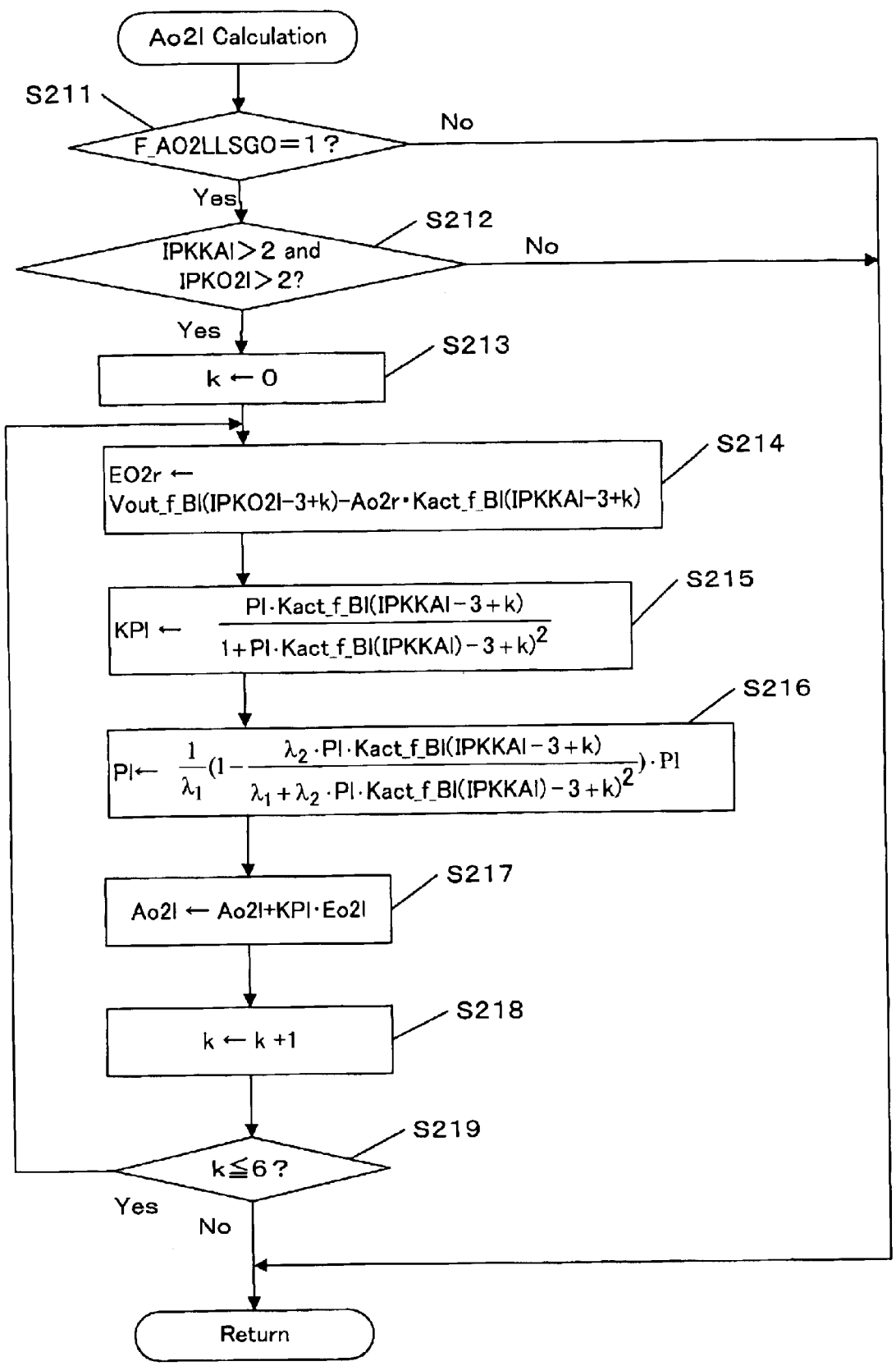
FIG. 18 is a flowchart showing a routine for calculating a lean side correlation coefficient in accordance with one embodiment of the present invention.
Figure 19:
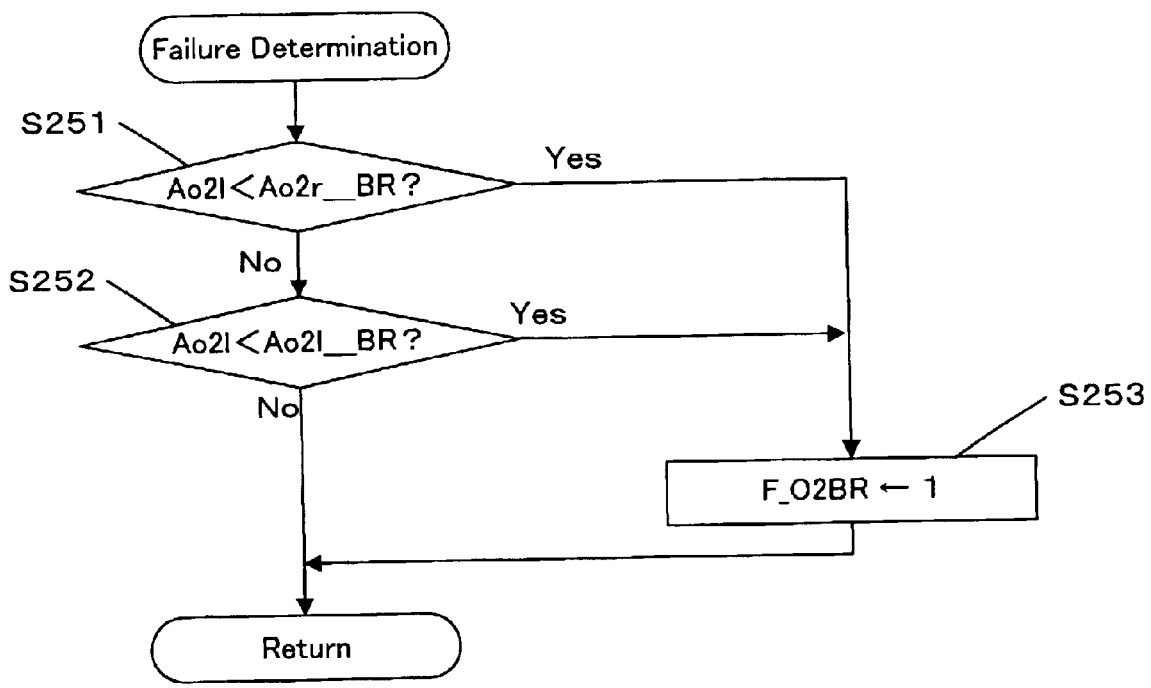
FIG. 19 is a flowchart showing a failure determination routine in accordance with one embodiment of the present invention.

If all of the answers of the determination steps S109 through S111 are "Yes", the process proceeds to step S112 so as to perform the failure detecting process. In step S112, a process for obtaining samples of the air-fuel ratio Kact_f and the sensor output Vout_f in the rich region is carried out (FIG. 15). In step S113, a process for obtaining samples of the air-fuel ratio Kact_f and the sensor output Vout_f in the lean region is carried out (FIG. 16). In step S114, the rich-side correlation coefficient Ao2R is calculated (FIG. 17). In step S115, the lean-side correlation coefficient Ao2l is calculated (FIG. 18). In step S116, it is determined whether the O2 sensor is normal or faulty based on the correlation coefficients Ao2R and Ao2l (FIG. 19).

FIG. 15 shows a flowchart of a process carried out in step S112 for obtaining rich-side samples. In step S120, the filtered air-fuel ratio Kact_f(k−d) in the current cycle is compared with the predetermined upper limit value Katct_f_H (see FIGS. 9 and 10). If the filtered air-fuel ratio Kact_f(k−d) is greater than the upper limit value Katct_f_H, it is determined whether the value of the continuation flag F_CKactH is one (S121). The continuation flag F_CKactH is a flag that is to be set to one when the process for extracting rich-side samples is completed.

In step S121, if the continuation flag F_CKactH is zero, it indicates that the process for extracting rich-side samples was not carried out in the previous cycle, proceeding to initialization steps S122 through S130. In the initialization steps, ring buffers Kact_f_Br(j) and Vout_f_Br(j) respectively provided for the Kact_f and Vout_f are cleared. In the embodiment, each of the ring buffers provides 20 slots.

In step S127, IPKKAr indicative of a buffer number of the buffer in which the peak value of the air-fuel ratio Kact_f is to be stored, and IPK02r indicative of a buffer number of the buffer in which the peak value of the sensor output Vout_f is to be stored are initialized to zero. In steps S129 and S130, Kact_f_peakr in which the peak value of Kact_f is to be set, and Vout_f_peakr in which the peak value of the Vout_f is to be set are initialized to zero.

In step S121, if the continuation flag F_CKactH is one, it indicates that the process for extracting rich-side samples was carried out in the previous cycle. The process proceeds to step S131, in which "i" is set to one. In steps S132 and S133, the ring buffers for Kact_f and Vout_f are shifted by one. That is, Kact_f stored in the (i−1)-th buffer Kact_f_Br(i−1) is shifted to the i-th buffer Kact_f_Br(i). Vout_f stored in the (i−1)-th buffer Vout_f_Br (i−1) is shifted to the i-th buffer Vout_f_Br(i). The shift operation is repeated until i=1 becomes i=20 (S137). Thus, the 0-th buffers Kact_f_Br(O) and Vout_f_Br(O) are emptied.

Since the ring buffers are shifted by one, one is added to the peak buffer numbers IPKKAr and IPK02r (S135 and S136). In steps S138 and S139, Kact_f(k−d) and Vout_f (k−d) in the current cycle are stored in the 0-th buffers that have been emptied by the shift operation.

In step S140, if Kact_f(k−d) in the current cycle is greater than the current peak value Kact_f_peakr, the peak value Kact_f_peakr is updated with Kact_f(k−d) (S141). Since the peak value is stored in the 0-th buffer, the peak buffer number IPKKAr is set to zero (S142).

In step S143, if Vout_f(k−d) in the current cycle is greater than the current peak value Vout_f_peakr, the peak value Vout_f_peakr is updated with Vout_f(k−d) (S144). Since the peak value is stored in the 0-th buffer, the peak buffer number IPK02r is set to zero (S145). Thus, the sample extraction process in the current cycle is completed. The continuation flag F_CKactH is set to 1 (S146).

Returning to step S120, if the filtered air-fuel ratio Kac_f(k−d) is lower than the upper limit value Katct_f_H, the value of the continuation flag F_CKactH is checked (S147). If the value of the continuation flag F_CKactH is one, a permission flag F_AO2RLSGO is set to one (S148) and the continuation flag F_CKactH is set to zero (S149) so as to calculate the correlation coefficient based on the rich-side samples extracted in previous cycles. In step S147, if the continuation flag F_CKactH is zero, the permission flag F_AO2RLSGO is set to zero (S150).

FIG. 16 is a flowchart of a process carried out in step S113 of FIG. 14 for obtaining lean-side samples. Since the process for obtaining lean-side samples is performed in a similar way to the process for obtaining rich-side samples shown in FIG. 15, detailed description thereof is omitted.

If the air-fuel ratio Kact_f(k−d) in the current cycle is less than the lower limit value Kact_f_L (see FIGS. 9 and 10) (S160) and the continuation flag F_CKactL is zero (S161), the initialization steps S162 through 170 are carried out. If the continuation flag F_CKactL is one in step S161, it indicates that the process for extracting lean-side samples was carried out in the previous cycle. In steps S171 to 177, ring buffers Kact_f_Bl(i) and Vout_f_Bl(i) provided for lean-side samples are shifted by one. In steps S178 and S179, the filtered air-fuel ratio Kact_f (K−d) and the filtered sensor output Vout_f(k−d) are stored in buffers Kact_fBl(0) and Vout_f_Bl(0), respectively. In steps S180 through S182, the lean side peak value Kact_f_peakl for the filtered air-fuel ratio Kact_f is updated, and the peak buffer number IPKKAl is set to zero. In steps S183 through S185, the lean side peak value Vout_f_peakl for the filtered sensor output Vout_f is updated, and the peak buffer number IP0KO2l is set to zero. In step S186, the continuation flag F_CKactL is set to one.

Returning to step S160, if the filtered air-fuel ratio Kact_f(k−d) in the current cycle is equal to or greater than the lower limit value Kact_f_L and the continuation flag F_CKactL is one (S187), then a permission flag F_AO2LLSGO is set to one (S188) and the continuation flag F_CKactL is set to zero (S189) so as to calculate the correlation coefficient based on the lean-side samples extracted in previous cycles. In step S187, if the continuation flag F_CKactL is zero, the permission flag F_AO2LLSGO is set to zero (S190).

FIG. 17 is a flowchart of a process carried out in step S114 of FIG. 14 for calculating the rich side correlation coefficient Ao2R. In the embodiment, the correlation coefficient Ao2R is calculated based on seven samples. One is a sample having the peak value, and the others are samples existing in the vicinity of the sample of the peak value. When the value of the permission flag F-AO2RLSGO is one, the process is started (S201).

In step S202, it is determined whether the peak buffer numbers IPKKAr and IPK02r are three or more. The peak buffer numbers IPKKAr and IPK02r indicate buffer numbers of the buffers in which the peak values are stored. If the peak buffer number IPKKAr is two or less, it indicates that the number of samples for the air-fuel ratio Kact_f is five or less. Similarly, if the peak buffer number IPK02r is two or less, it indicates that the number of samples for the sensor output Vout_f is five or less. If the number of samples is too small, the statistical process may not be carried out appropriately. Therefore, if the peak buffer number IPKKAr or IPK02r is two or less, the process exits the routine.

In step S203, "k" is set to zero. In steps S204 through 207, the statistical process is carried out using the successive least squares method. In step S204, the error Eo2r is determined in accordance with the equation (6). Ao2r shown in step S204 indicates the rich side correlation coefficient calculated in the previous cycle. In step S205, the gain coefficient KPr is determined in accordance with the equation (7). "Pr" shown in step S205 has been calculated in the previous cycle in accordance with the equation (8). In step S206, "Pr" that is to be used in the next cycle is calculated. In step S207, the rich side correlation coefficient Ao2r is calculated using the error Eo2r and the gain coefficient Kpr calculated in steps S204 and S205 in accordance with the equation (5).

The calculation steps S204 through S207 are carried out until k becomes equal to six in step S209. For example, if the peak value is stored in the fourth buffer, samples stored in the first to seventh buffers are processed.

FIG. 18 is a flowchart of a process carried out in step S115 of FIG. 14 for calculating the lean side correlation coefficient Ao2l. Since the process for calculating the lean side correlation coefficient is performed in a similar way to the process for calculating the rich side correlation coefficient, detailed description thereof is omitted. The successive least squares method is applied to seven samples. One is a sample having the peak value (maximum absolute value), three are samples existing on the left side of the peak value, and three are samples existing on the right side of the peak value. Thus, the correlation coefficient Ao2l is determined.

FIG. 19 is a flowchart of a process for determining a failure of the O2 sensor based on the correlation coefficients Ao2r and Ao2l. In step S251, if the rich side correlation coefficient Ao2r is less than the predetermined value Ao2r_BR, it is determined that the O2 sensor is faulty. In step S252, if the lean side correlation coefficient Ao2l is less than the predetermined value Ao2r_BR, it is determined that the O2 sensor is faulty. If it is determined that the O2 sensor is faulty, the flag F_O2BR is set to one. If the answers of the determination steps S251 and S252 are "No", it is determined that the O2 sensor is normal. When the O2 sensor is normal, the process exits the routine without setting the failure flag F_O2BR to one.

Initial values of the correlation coefficients Ao2r and Ao2l may be zero. Alternatively, values stored in a backup RAM at the time when the engine stops in the previous driving cycle may be used as the initial values.

The invention may be applied to an engine to be used in a vessel-propelling machine such as an outboard motor in which a crankshaft is disposed in the perpendicular direction.

What is claimed is:

1. An apparatus for detecting a failure of an exhaust gas sensor disposed downstream of a catalyst converter in an exhaust manifold of an engine, the apparatus comprising a control unit configured to:

select from outputs of the exhaust gas sensor a first output having a local maximum amplitude value;

select from outputs of an air-fuel sensor a second output having a local maximum amplitude value, the air fuel ratio sensor disposed upstream of the catalyst converter;

determine a ratio between the local maximum amplitude value of the first output and the local maximum amplitude value of the second output; and detect the failure of the exhaust gas sensor based on the ratio.

2. The apparatus of claim 1, wherein the local maximum amplitude value of the first output is greater than a predetermined value; and the local maximum amplitude value of the second output is greater than a predetermined value.

3. The apparatus of claim 1, wherein the control unit is further configured to apply a statistical process to the ratio using a successive least squares method, wherein the failure of the exhaust gas sensor is detected based on the statistically processed ratio.

4. The apparatus of claim 1, wherein the control unit is further configured to apply a statistical process to both the first output of the exhaust gas sensor and the second output of the air-fuel ratio sensor using a successive least squares method, wherein the ratio is determined as a ratio between the statistically processed first output and the statistically processed second output.

5. The apparatus of claim 1, wherein the first output of the exhaust gas sensor and the second output of the air-fuel ratio sensor are acquired when a vehicle on which the engine is mounted is at cruise.

6. The apparatus of claim 1, wherein the first output of the exhaust gas sensor and the second output of the air-fuel ratio sensor are acquired when the engine is in a predetermined operating state.

7. The apparatus of claim 1, further comprising a filter for filtering the first output of the exhaust gas sensor and the second output of the air-fuel ratio sensor, wherein the ratio is determined as a ratio between the filtered first output and the filtered second output.

8. The apparatus of claim 7, wherein the filter comprises a band-pass filter.

9. The apparatus of claim 7, wherein the filter has characteristics of passing frequency components that are influenced by deterioration of the exhaust gas sensor, and that are different from frequency components influenced by deterioration of the catalyst converter.

10. An apparatus for detecting a failure of an exhaust gas sensor disposed downstream of a catalyst converter in an exhaust manifold of an engine, the apparatus comprising a control unit configured to:

determine a ratio between an amplitude value of a first output of the exhaust gas sensor and an amplitude value of a second output of an air-fuel ratio sensor, the air-fuel ratio sensor disposed upstream of the catalyst converter; and detect the failure of the exhaust gas sensor based on the ratio, wherein the control unit is further configured to sample outputs of the exhaust gas sensor;

identify from the samples obtained from the exhaust gas sensor a first sample having a local maximum amplitude value;

select samples in the vicinity of the first sample;

sample outputs of the air-fuel ratio sensor;

identify from the samples obtained from the air-fuel sensor a second sample having a local maximum amplitude value;

select samples in the vicinity of the second sample; and determine the ratio based on a first set of samples and a second set of samples, the first set of samples including the first sample and the selected samples in the vicinity of the first sample, the second set of samples including the second sample and the selected samples in the vicinity of the second sample.

11. The apparatus of claim 10, wherein the local maximum amplitude value of the first output is greater than a predetermined value and the local maximum amplitude value of the second output is greater than a predetermined value.

12. The apparatus of claim 10, wherein the control unit is further configured to apply a statistical process to the ratio using a successive least squares method, wherein the failure of the exhaust gas sensor is detected based on the statistically processed ratio.

13. The apparatus of claim 10, wherein the control unit is further configured to apply a statistical process to both the first output of the exhaust gas sensor and the second output of the air-fuel ratio sensor using a successive least squares method, wherein the ratio is determined as a ratio between the statistically processed first output and the statistically processed second output.

14. The apparatus of claim 10, wherein the first output of the exhaust gas sensor and the second output of the air-fuel ratio sensor are acquired when a vehicle on which the engine is mounted is at cruise.

15. The apparatus of claim 10, wherein the first output of the exhaust gas sensor and the second output of the air-fuel ratio sensor are acquired when the engine is in a predetermined operating state.

16. The apparatus of claim 10, further comprising a filter for filtering the first output of the exhaust gas sensor and the second output of the air-fuel ratio sensor, wherein the ratio is determined as a ratio between the filtered first output and the filtered second output.

17. The apparatus of claim 16, wherein the filter comprises a band-pass filter.

18. The apparatus of claim 16, wherein the filter has characteristics of passing frequency components that are influenced by deterioration of the exhaust gas sensor, and that are different from frequency components influenced by deterioration of the catalyst converter.

19. A method for detecting a failure of an exhaust gas sensor disposed downstream of a catalyst converter in an exhaust manifold of an engine, the method comprising the steps of:

selecting from outputs of the exhaust gas sensor a first output having a local maximum amplitude value;

selecting from outputs of an air-fuel sensor a second output having a local maximum amplitude value, the air fuel ratio sensor disposed upstream of the catalyst converter;

determining a ratio between the local maximum amplitude value of the first output and the local maximum amplitude value of the second output; and detecting the failure of the exhaust gas sensor based on the ratio.

20. The method of claim 19, wherein the local maximum amplitude value of the first output is greater than a predetermined value; and the local maximum amplitude value of the second output is greater than a predetermined value.

21. The method of claim 19, further comprising the step of applying a statistical process to the ratio using a successive least squares method, wherein the failure of the exhaust gas sensor is detected based on the statistically processed ratio.

22. The method of claim 19, further comprising the step of applying a statistical process to both the first output of the exhaust gas sensor and the second output of the air-fuel ratio sensor using a successive least squares method, wherein the ratio is determined as a ratio between the statistically processed first output and the statistically processed second output.

23. The method of claim 19, further comprising the step of acquiring the first output of the exhaust gas sensor and the second output of the air-fuel ratio sensor when a vehicle on which the engine is mounted is at cruise.

24. The method of claim 19, further comprising the step of acquiring the first output of the exhaust gas sensor and the second output of the air-fuel ratio sensor when the engine is in a predetermined operating state.

25. The method of claim 19, further comprising the step of filtering the first output of the exhaust gas sensor and the second output of the air-fuel ratio sensor, wherein the ratio is determined as a ratio between the filtered first output and the filtered second output.

26. The method of claim 25, wherein the filter comprises a band-pass filter.

27. The method of claim 25, wherein the filter has characteristics of passing frequency components that are influenced by deterioration of the exhaust gas sensor, and that are different from frequency components influenced by deterioration of the catalyst converter.

28. A method for detecting a failure of an exhaust gas sensor disposed downstream of a catalyst converter in an exhaust manifold of an engine, the method comprising the steps of:

determining a ratio between an amplitude value of a first output of the exhaust gas sensor and an amplitude value of a second output of an air-fuel ratio sensor, the air-fuel ratio sensor disposed upstream of the catalyst converter; and detecting the failure of the exhaust gas sensor based on the ratio, wherein the step of determining a ratio further comprises the steps of sampling outputs of the exhaust gas sensor;

identifying from the samples obtained from the exhaust gas sensor a first sample having a local maximum amplitude value;

selecting samples in the vicinity of the first sample;

sampling outputs of the air-fuel ratio sensor;

identifying from the samples obtained from the air-fuel sensor a second sample having a local maximum amplitude value; and selecting samples in the vicinity of the second sample; and determining the ratio based on a first set of samples and a second set of samples, the first set of samples including the first sample and the selected samples in the vicinity of the first sample, the second set of samples including the second sample and the selected samples in the vicinity of the second sample.

29. A computer program stored on a computer readable medium for use in detecting a failure of an exhaust gas sensor disposed downstream of a catalyst converter in an exhaust manifold of an engine, the computer program comprising:

program code for selecting from outputs of the exhaust gas sensor a first output having a local maximum amplitude value;

program code for selecting from outputs of an air-fuel sensor a second output having a local maximum amplitude value, the air fuel ratio sensor disposed upstream of the catalyst converter;

program code for determining a ratio between the local maximum amplitude value of the first output and the local maximum amplitude value of the second output; and program code for detecting the failure of the exhaust gas sensor based on the ratio.

30. The computer program of claim 29, wherein
the local maximum amplitude value of the first output is greater than a predetermined value; and
the local maximum amplitude value of the second output is greater than a predetermined value.

31. The computer program of claim 29, further comprising program code for applying a statistical process to the ratio using a successive least squares method,
wherein the failure of the exhaust gas sensor is detected based on the statistically processed ratio.

32. The computer program of claim 29, further comprising program code for applying a statistical process to both the first output of the exhaust gas sensor and the second output of the air-fuel ratio sensor using a successive least squares method,
wherein the ratio is determined as a ratio between the statistically processed first output and the statistically processed second output.

33. The computer program of claim 29,
wherein the first output of the exhaust gas sensor and the second output of the air-fuel ratio sensor are acquired when a vehicle on which the engine is mounted is at cruise.

34. The computer program of claim 29,
wherein the first output of the exhaust gas sensor and the second output of the air-fuel ratio sensor are acquired when the engine is in a predetermined operating state.

35. The computer program of claim 29, further comprising program code for filtering the first output of the exhaust gas sensor and the second output of the air-fuel ratio sensor,
wherein the ratio is determined as a ratio between the filtered first output and the filtered second output.

36. The computer program of claim 35, wherein the filter comprises a band-pass filter.

37. The computer program of claim 35, wherein the filter has characteristics of passing frequency components that are influenced by deterioration of the exhaust gas sensor, and that are different from frequency components influenced by deterioration of the catalyst converter.

38. A computer program stored on a computer readable medium for use in detecting a failure of an exhaust gas sensor disposed downstream of a catalyst converter in an exhaust manifold of an engine, the computer program comprising:

program code for determining a ratio between an amplitude value of a first output of the exhaust gas sensor and an amplitude value of a second output of an air-fuel ratio sensor, the air-fuel ratio sensor disposed upstream of the catalyst converter; and program code for detecting the failure of the exhaust gas sensor based on the ratio, wherein program code for determining a ratio further includes program code for sampling outputs of the exhaust gas sensor;

program code for identifying from the samples obtained from the exhaust gas sensor a first sample having a local maximum amplitude value;

program code for selecting samples in the vicinity of the first sample;

program code for sampling outputs of the air-fuel ratio sensor;

program code for identifying from the samples obtained from the air-fuel sensor a second sample having a local maximum amplitude value;

program code for selecting samples in the vicinity of the second sample; and program code for determining the ratio based on a first set of samples and a second set of samples, the first set of samples including the first sample and the selected samples in the vicinity of the first sample, the second set of samples including the second sample and the selected samples in the vicinity of the second sample.

* * * * *